US011730557B2

(12) United States Patent
O'Flynn et al.

(10) Patent No.: US 11,730,557 B2
(45) Date of Patent: *Aug. 22, 2023

(54) PACKAGES FOR MEDICAL DEVICES AND MEDICAL DEVICE ASSEMBLIES

(71) Applicant: Hollister Incorporated, Libertyville, IL (US)

(72) Inventors: Padraig M. O'Flynn, Ballina (IL); Brendan J. Heneghan, Westport (IE); Thomas Renehan, Ballina (IE); Jennifer Munnelly, Ballina (IE); Robert A. Greynolds, Northbrook, IL (US); Dmitry Sheremetiev, Oranmore (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/538,725

(22) Filed: Nov. 30, 2021

(65) Prior Publication Data

US 2022/0133426 A1    May 5, 2022

Related U.S. Application Data

(63) Continuation of application No. 16/619,609, filed as application No. PCT/US2018/036633 on Jun. 8, 2018, now Pat. No. 11,234,786.

(Continued)

(51) Int. Cl.
| | |
|---|---|
| *A61B 50/30* | (2016.01) |
| *B65D 75/32* | (2006.01) |
| *B65D 75/58* | (2006.01) |
| *B65D 81/22* | (2006.01) |
| *A61B 50/00* | (2016.01) |
| *A61M 25/00* | (2006.01) |

(52) U.S. Cl.
CPC ............ *A61B 50/30* (2016.02); *B65D 75/326* (2013.01); *B65D 75/5827* (2013.01); *B65D 81/22* (2013.01); *A61B 2050/002* (2016.02); *A61B 2050/0065* (2016.02); *A61M 25/002* (2013.01)

(58) Field of Classification Search
CPC .. B65D 81/22; B65D 75/5827; B65D 75/326; A61B 50/30; A61B 2050/0065; A61M 5/002
USPC ........................................ 206/364, 365, 210
See application file for complete search history.

(56) References Cited

U.S. PATENT DOCUMENTS

| | | |
|---|---|---|
| 3,035,691 A | 5/1962 | Kai |
| 4,723,301 A | 2/1988 | Chang |

(Continued)

FOREIGN PATENT DOCUMENTS

| | | |
|---|---|---|
| EP | 3023357 A1 | 5/2016 |
| WO | 199611146 A1 | 4/1996 |

OTHER PUBLICATIONS

International Search Report and Written Opinion of the International Searching Authority dated Nov. 7, 2018 for International Application No. PCT/US2018/036633.

*Primary Examiner* — Steven A. Reynolds
(74) *Attorney, Agent, or Firm* — Cook Alex Ltd.

(57) ABSTRACT

A package for containing a medical device including peel stops located in the first side seal zone and the second side seal zone of a peripheral seal of package, wherein the first and second peel-stops limit peeling of the first and second side seal zones of the peripheral seal.

17 Claims, 19 Drawing Sheets

Related U.S. Application Data

(60) Provisional application No. 62/517,352, filed on Jun. 9, 2017.

(56) References Cited

U.S. PATENT DOCUMENTS

| | | |
|---|---|---|
| 5,217,772 A | 6/1993 | Brown et al. |
| 5,895,374 A | 4/1999 | Rødsten |
| 5,938,013 A | 8/1999 | Palumbo et al. |
| 6,415,921 B2 | 7/2002 | Ye et al. |
| 6,578,709 B1 | 6/2003 | Kavanagh et al. |
| 6,726,054 B2 | 4/2004 | Fagen et al. |
| 6,767,604 B2 | 7/2004 | Muir, Jr. et al. |
| 6,887,230 B2 | 5/2005 | Kubalak et al. |
| 7,104,419 B2 | 9/2006 | Fagen et al. |
| 7,334,679 B2 | 2/2008 | Givens, Jr. |
| 7,380,658 B2 | 6/2008 | Murray et al. |
| 7,770,726 B2 | 8/2010 | Murray et al. |
| 7,770,728 B2 | 8/2010 | Kærn |
| 8,459,455 B2 | 6/2013 | Frojd |
| 8,727,117 B2 | 5/2014 | Maasarani |
| 8,740,863 B2 | 6/2014 | Nestenborg et al. |
| 8,808,275 B2 | 8/2014 | Gustavsson |
| 8,870,848 B2 | 10/2014 | Hiniduma-Lokuge et al. |
| 8,986,265 B2 | 3/2015 | Nestenborg et al. |
| 9,144,659 B2 | 9/2015 | Tanghoj |
| 11,234,786 B2 * | 2/2022 | O'Flynn ............ A61M 5/002 |
| 2001/0040110 A1 * | 11/2001 | Ye ..................... A61B 50/30 |
| | | 206/363 |
| 2008/0063325 A1 | 3/2008 | Miller et al. |
| 2008/0155941 A1 | 7/2008 | Williams-Hartman |
| 2011/0000806 A1 | 1/2011 | Kaern |
| 2011/0295239 A1 * | 12/2011 | Gustavsson ........ A61M 25/002 |
| | | 604/544 |
| 2013/0153446 A1 | 6/2013 | Utas et al. |
| 2013/0161208 A1 | 6/2013 | Gustavsson |
| 2014/0066904 A1 | 3/2014 | Young |
| 2015/0133898 A1 | 5/2015 | Murray et al. |
| 2016/0038713 A1 * | 2/2016 | Kearns ............ A61M 25/0111 |
| | | 206/364 |
| 2016/0325903 A1 | 11/2016 | Doerschner et al. |
| 2017/0137196 A1 | 5/2017 | Tinoco et al. |
| 2017/0216557 A1 | 8/2017 | Kearns et al. |
| 2017/0274176 A1 | 9/2017 | Kelly et al. |
| 2017/0326334 A1 | 11/2017 | Terry |
| 2017/0355504 A1 * | 12/2017 | Cardin .................. B65B 9/02 |

* cited by examiner

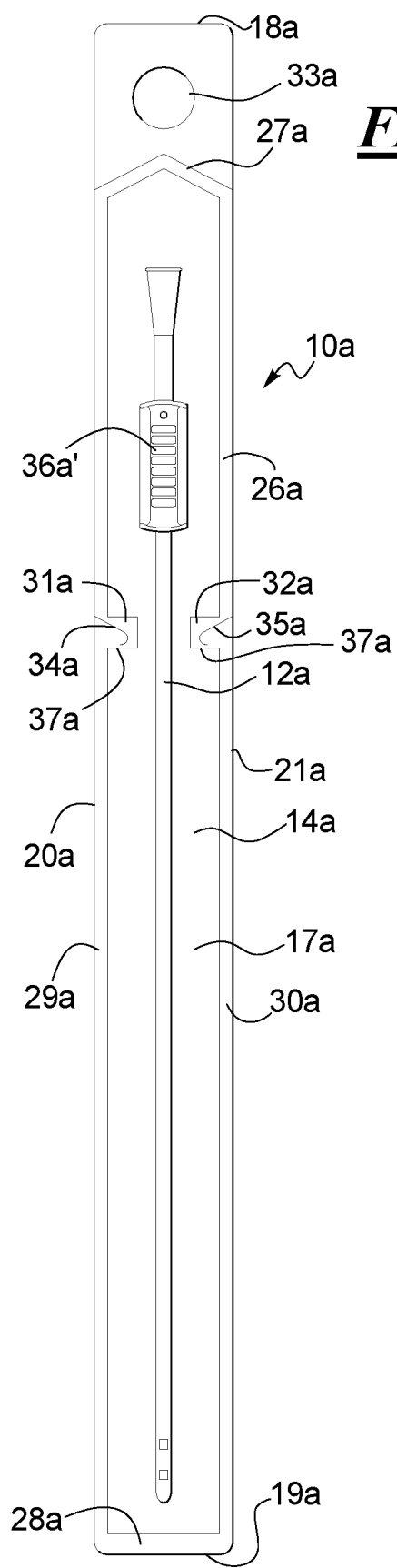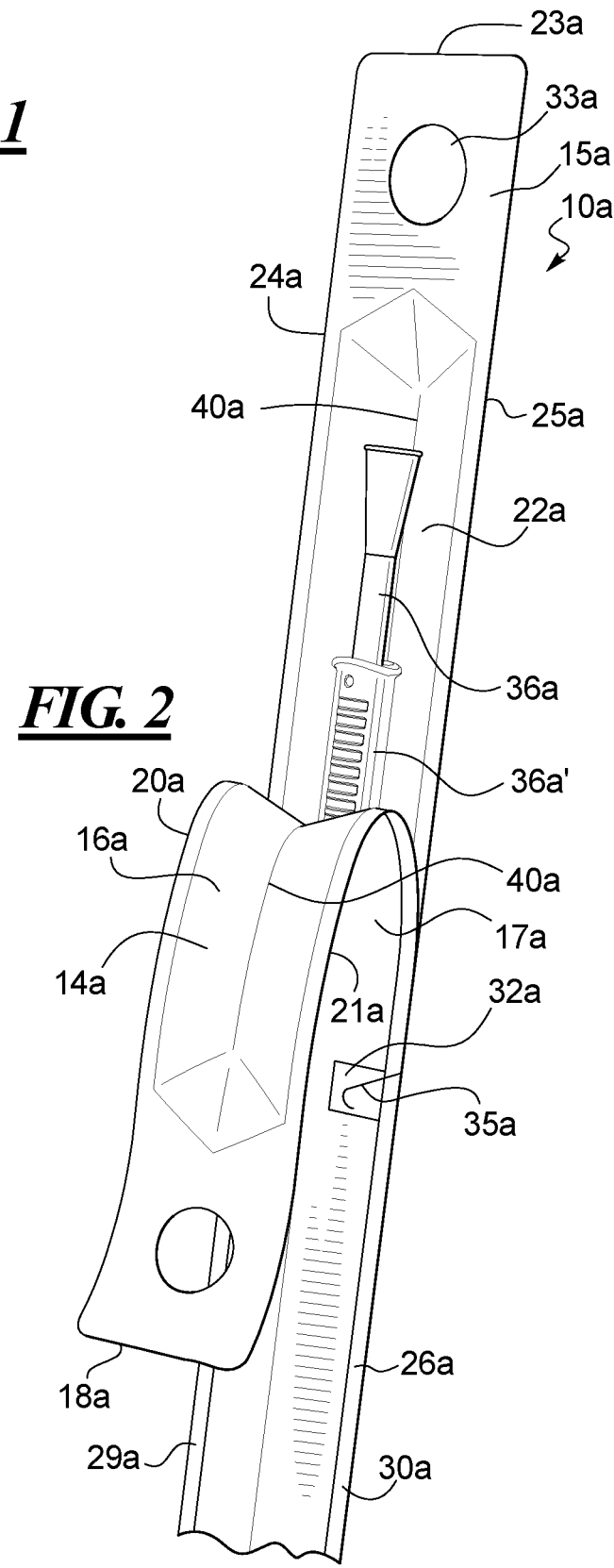

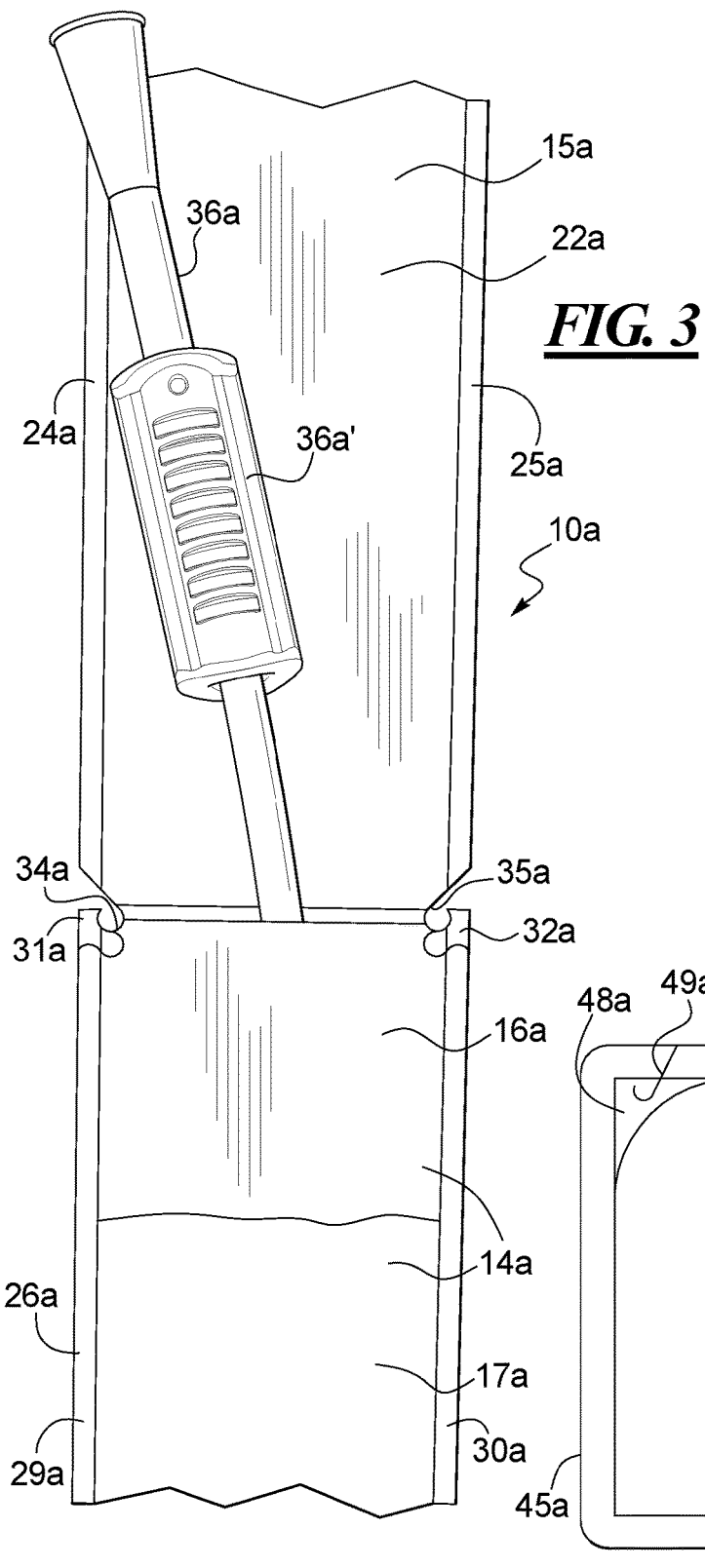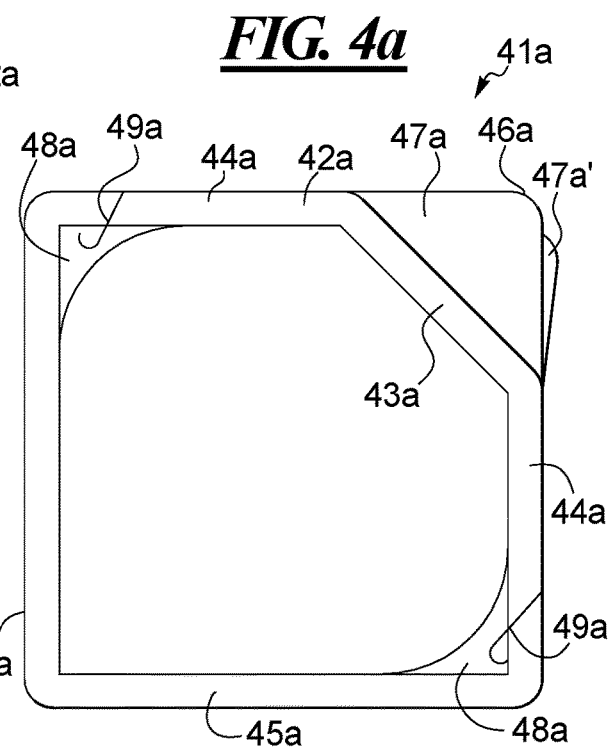

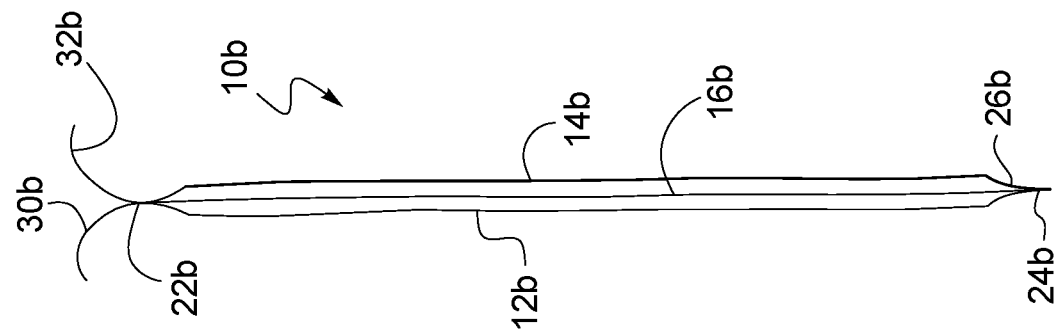
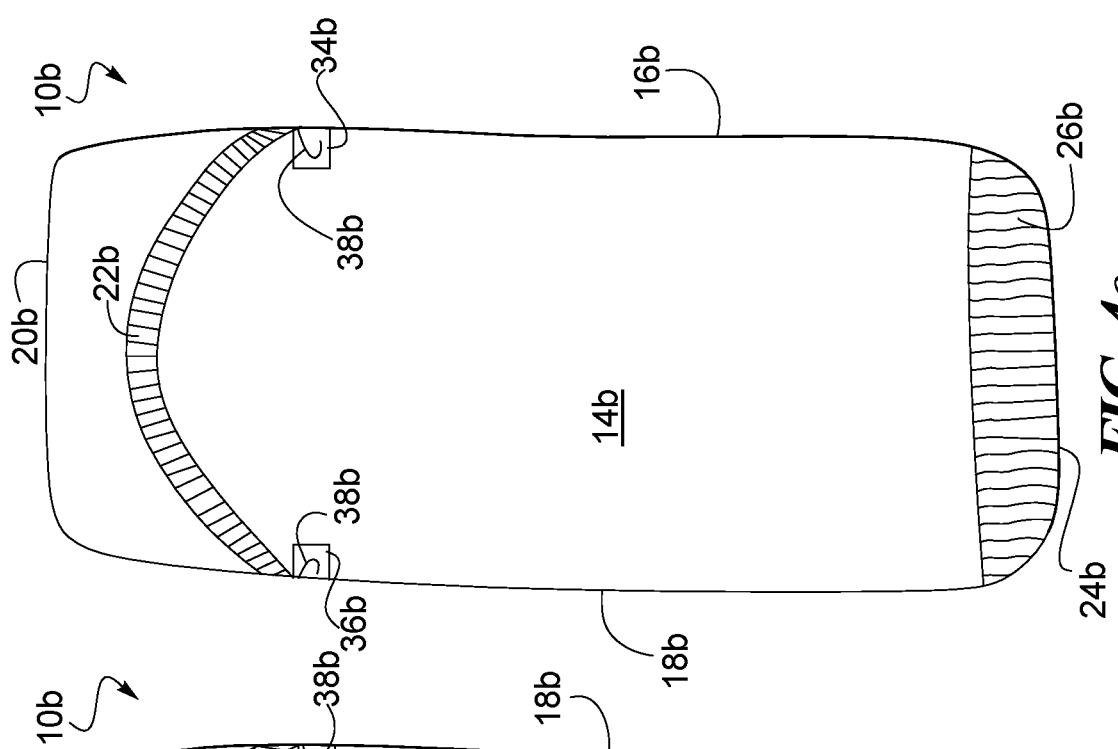
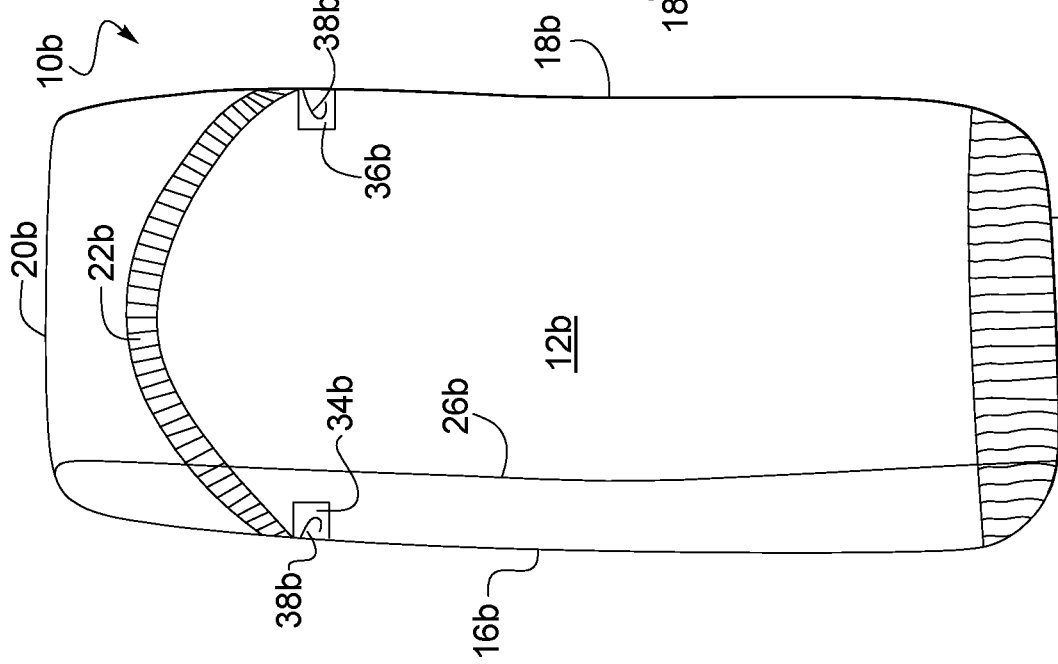

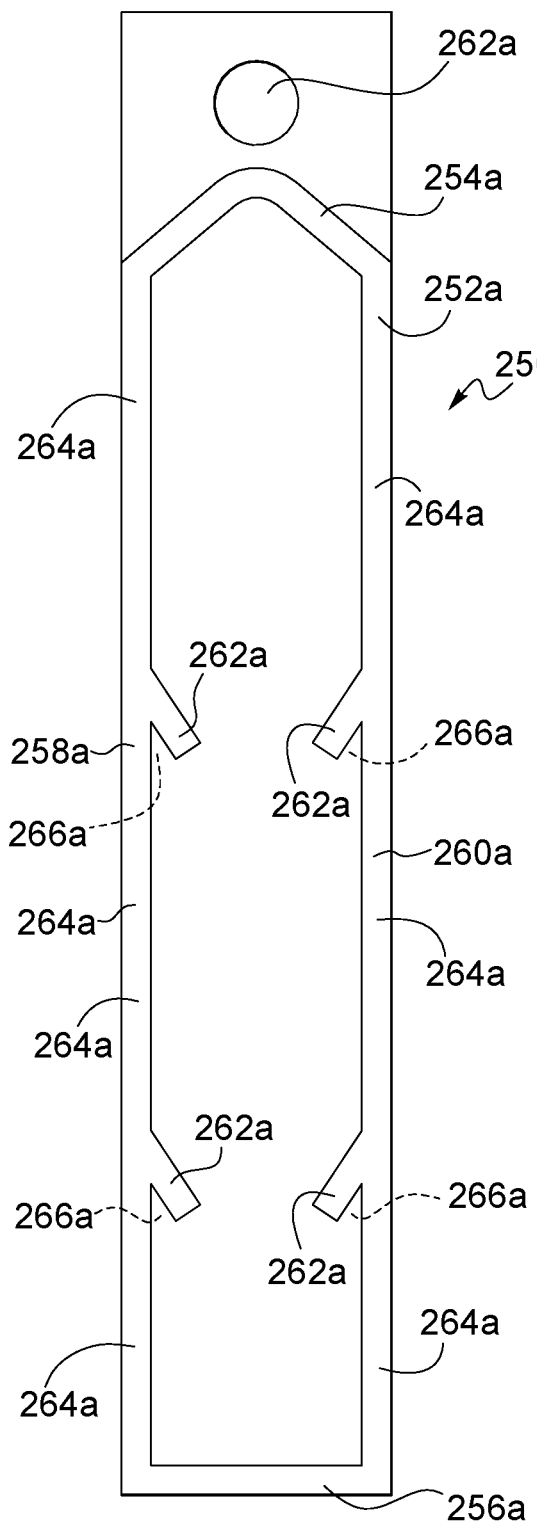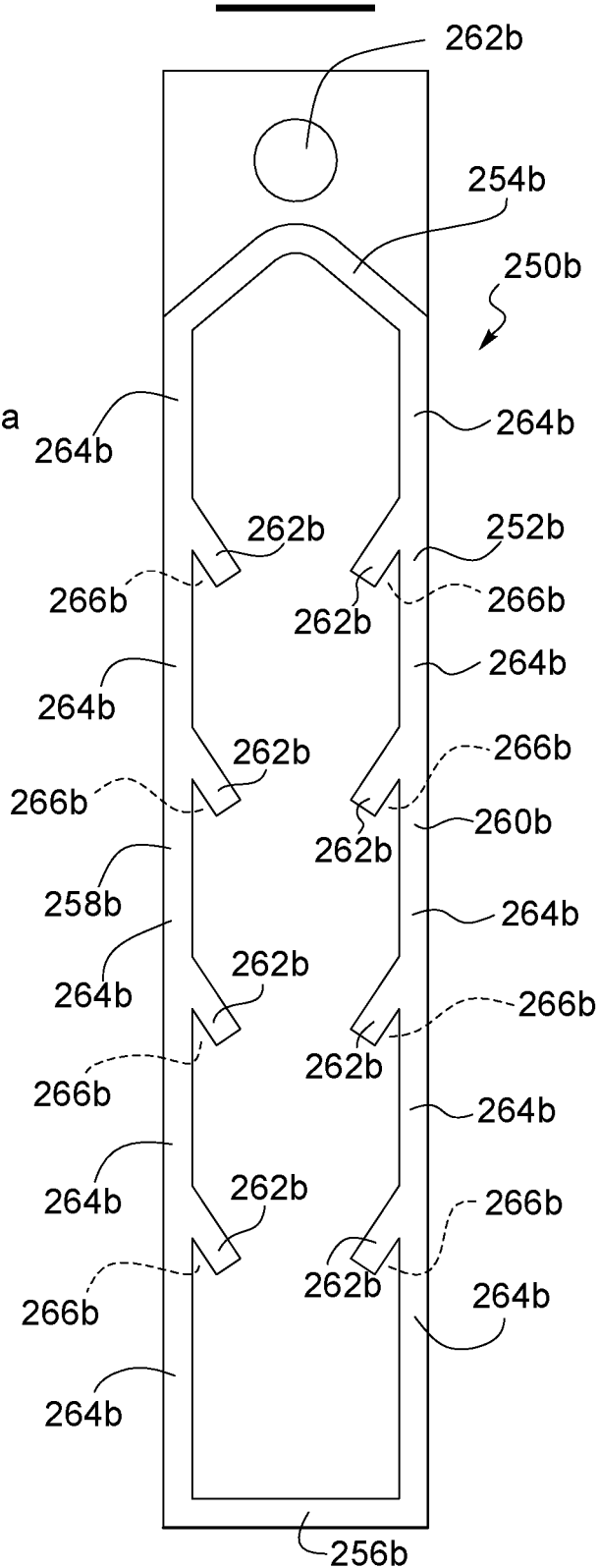

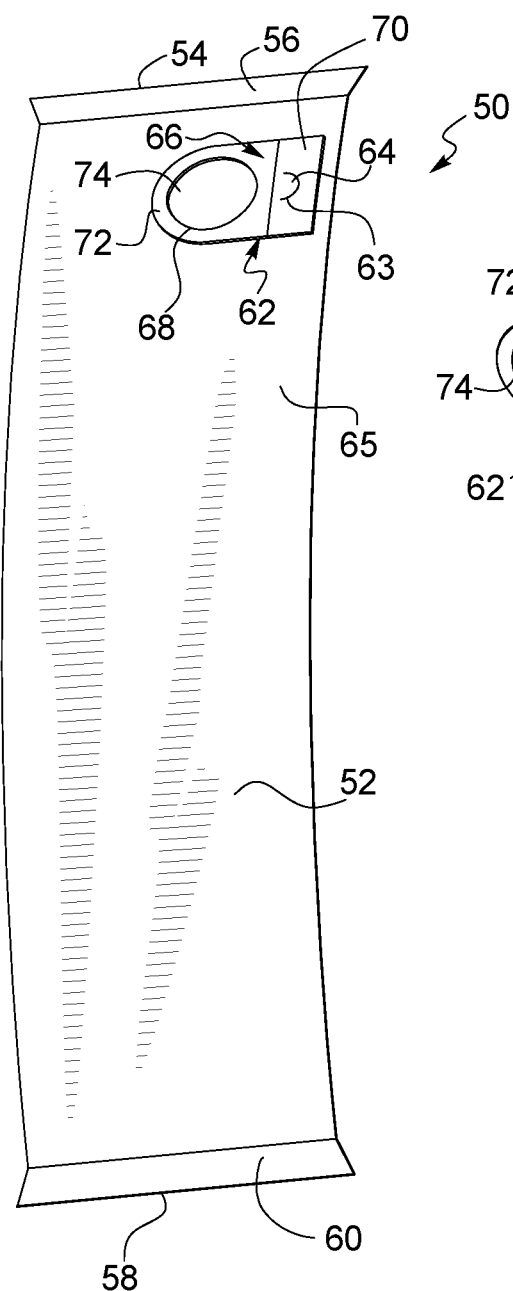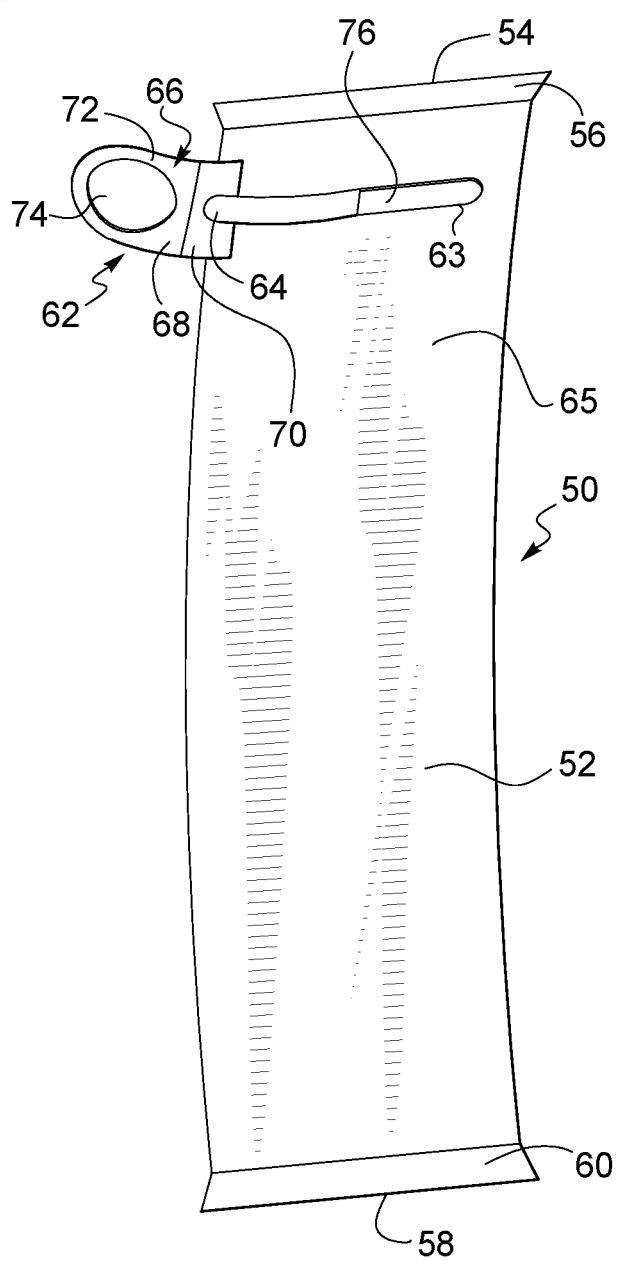

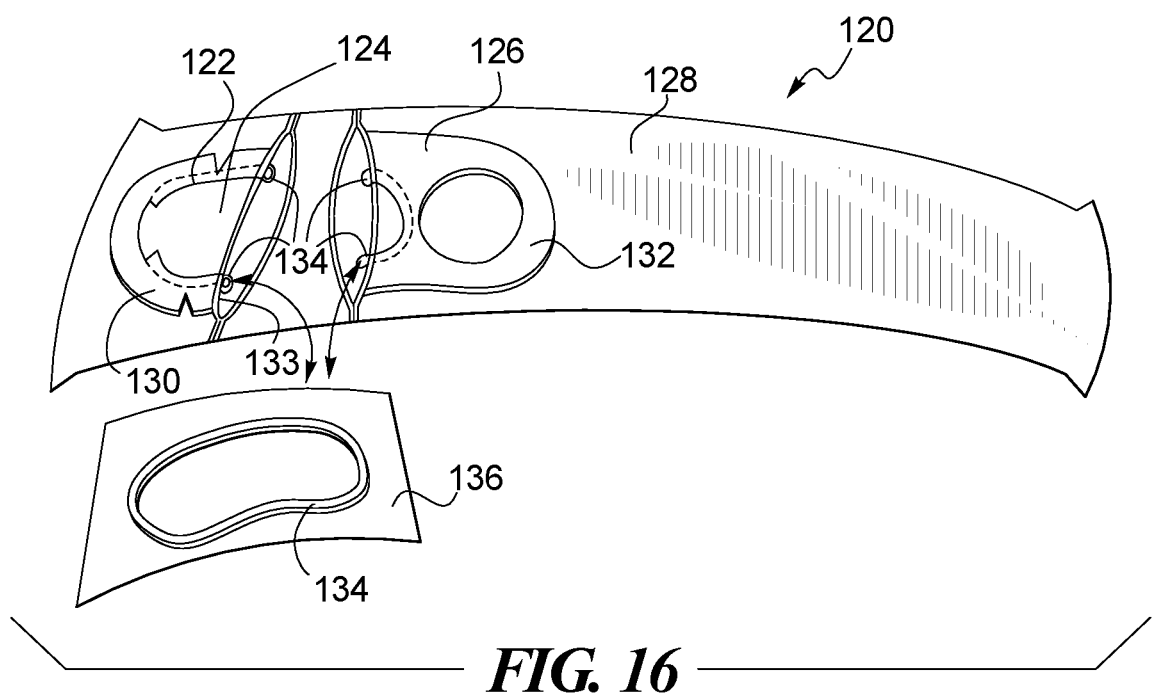
FIG. 16
FIG. 17
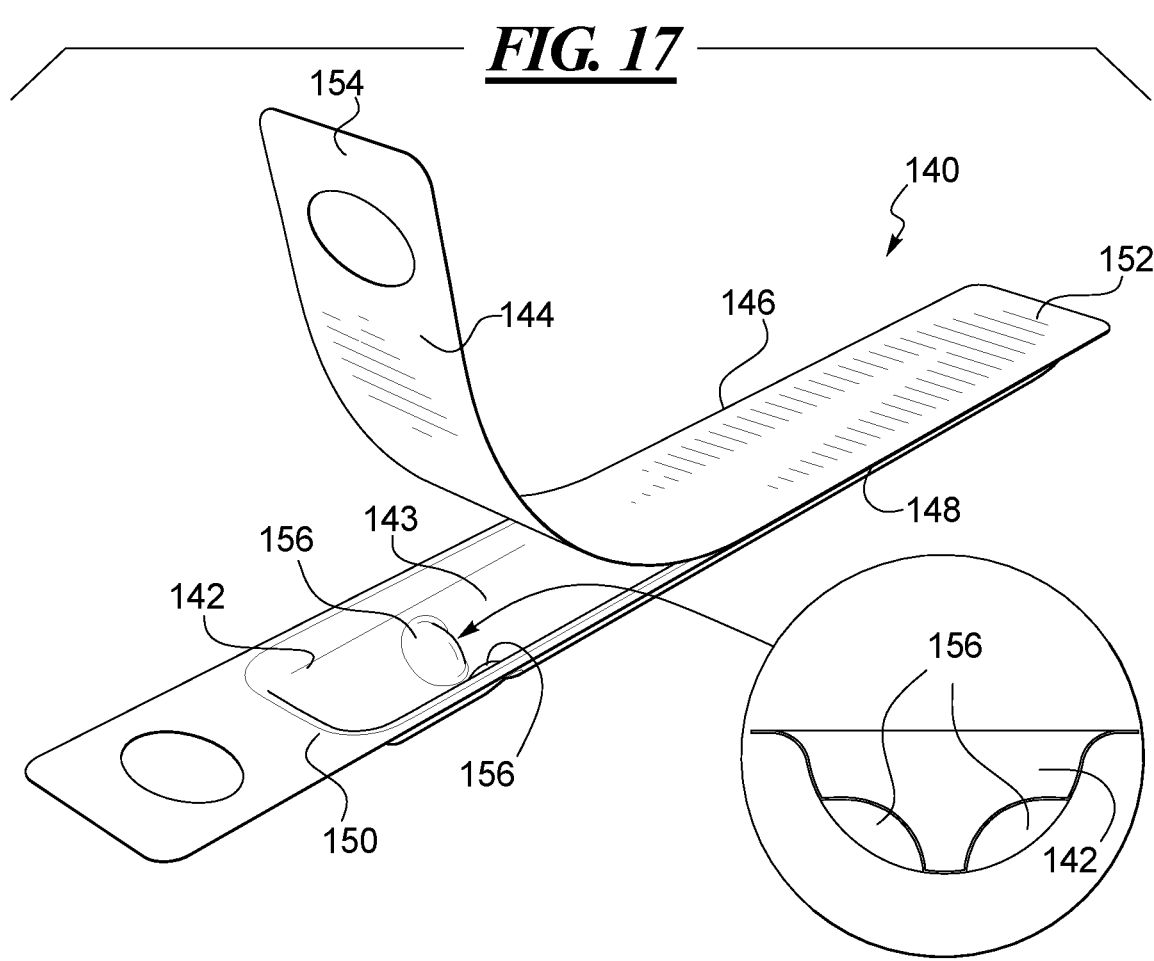

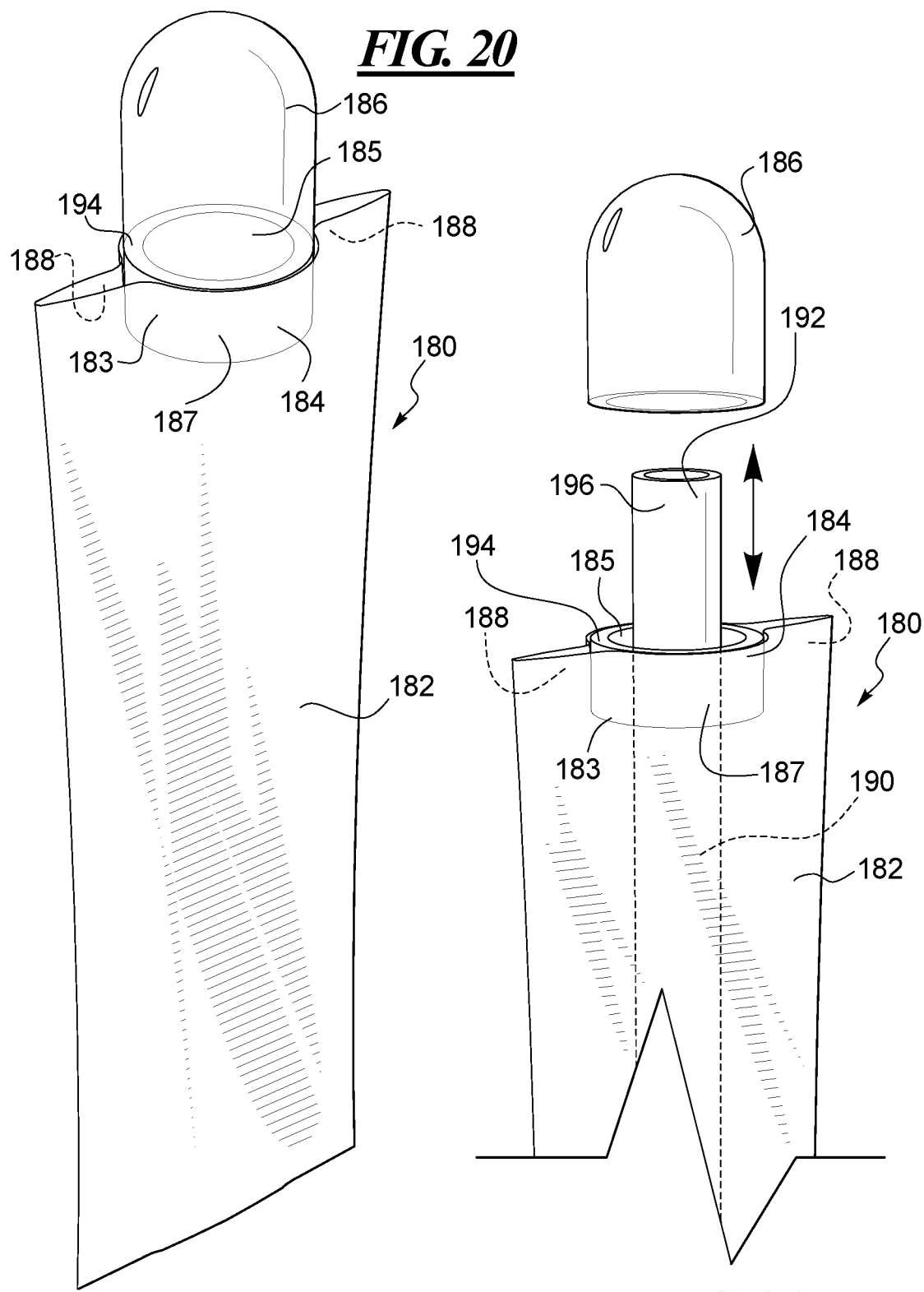

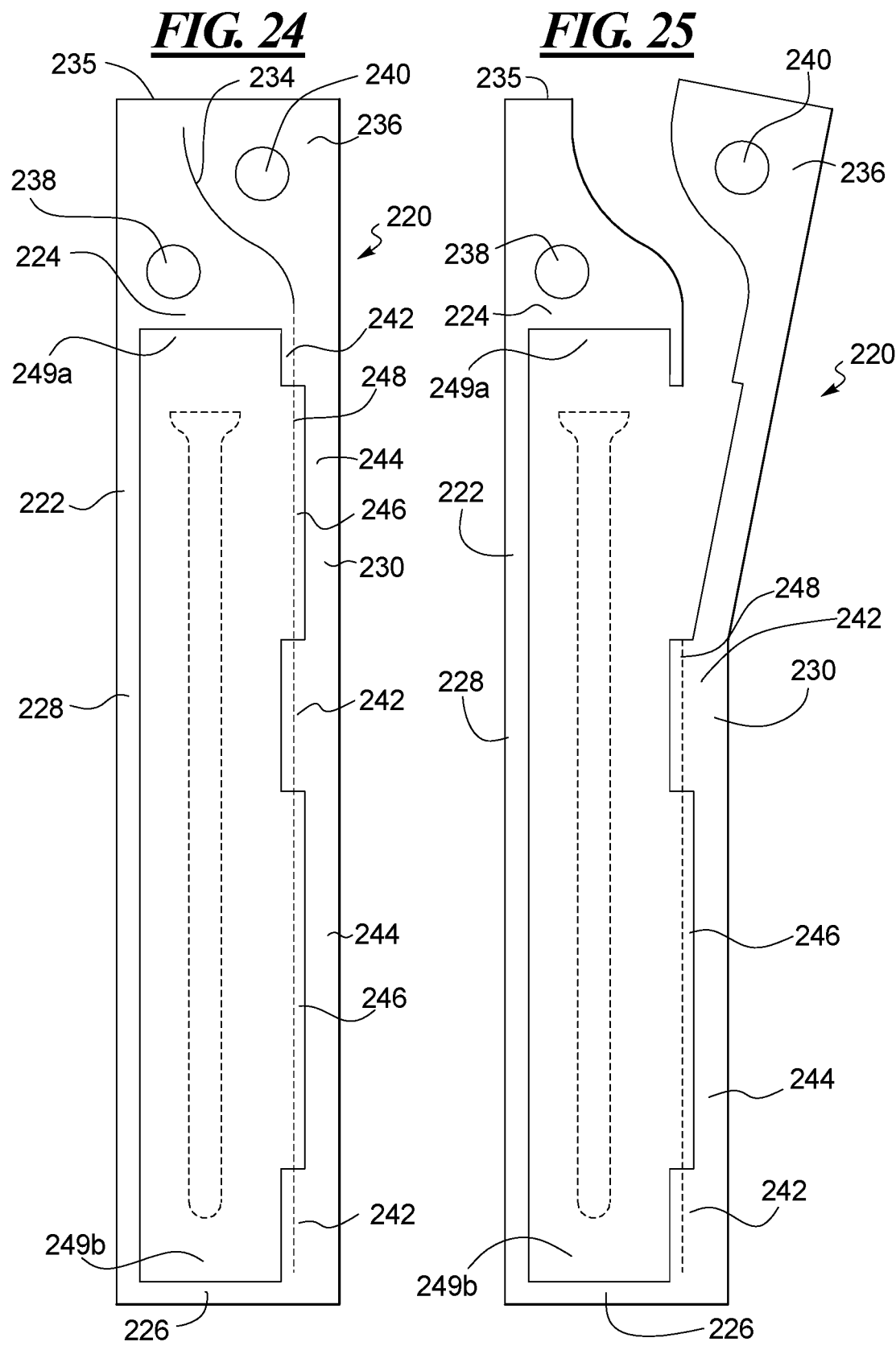

PACKAGES FOR MEDICAL DEVICES AND MEDICAL DEVICE ASSEMBLIES

RELATED APPLICATION

The present application is a continuation of U.S. patent application Ser. No. 16/619,609, filed Dec. 5, 2019, which is the U.S. National Stage of PCT/US2018/36633, filed Jun. 8, 2018, which claims the benefit and priority of U.S. Provisional Patent Application No. 62/517,352, filed Jun. 9, 2017, all of which are hereby incorporated herein by reference.

FIELD OF THE DISCLOSURE

The present disclosure generally relates to packages for medical devices, and more particularly, to packages for urinary catheters. Even more particularly, the present disclosure relates to packages that are configured to contain a hydrophilic catheter and a hydration liquid for activating the hydrophilic catheter.

BACKGROUND

It is desirable for medical devices that are inserted into the body to have a lubricated or lubricious outer surface to facilitate insertion into and/or removal of the medical device from the body. Such devices may include, for example, urinary catheters, endoscopes, cardiovascular catheters, syringes, vascular stents, etc. Such medical devices may have a hydrophilic coating or layer disposed on an outer surface thereof. Hydrophilic coatings are becoming the preferred method of providing lubricious surfaces because of their high lubricity and ease of use. Hydrophilic coatings become slippery or lubricous when wetted with a hydration medium, such as saline or liquid or vapor water. The hydrated lubricous hydrophilic coating eases insertion and removal of the device, which can result in minimizing soft tissue damage and reducing overall discomfort during use of the medical device.

When a hydrophilically coated medical device is used, the hydrophilic coating is hydrated with a hydration medium prior to use to activate the hydrophilic coating. For example, the user may immerse or otherwise contact the hydrophilic coating with a hydration liquid to hydrate or activate the coating. It is also becoming quite common to provide a package that includes the medical device and hydration liquid within the cavity of the package. In one type of package, the hydration liquid may be loose within the package and in contact with the hydrophilic medical device during storage and distribution of the package. In another type of package, the medical device and an openable sachet or pouch that contains the hydration liquid may be located within the package. In this second type of package the user bursts open the sachet within the package just prior to use. After the sachet is burst open, the hydration liquid is released and is loose within the package wherein it contacts and hydrates the hydrophilic medical device.

In packages that contain a hydration liquid, the hydration liquid is either initially loose within the package or becomes loose after being released from a sachet. Because these packages include loose hydration liquid at the time of opening the package, there is a risk of hydration liquid spillage upon opening the package and removal of the medical device from the package. Such spillage may cause a mess, which can require clean up. In some instances, the hydration liquid may include additives that can undesirably stain the clothes of the user.

Therefore, there remains a need for improved medical device packages for containing a medical device and a fluid, wherein the package assists in reducing the risk of fluid spillage.

SUMMARY

In one aspect, a top peel open package wherein the package initial opens along the top and the proceeds to open along the sides of the package. In a four side sealed package that includes two sheets sealed together, the package may open by peeling apart the two sheets at the top seal and then peeling along the side seals. In a flow-wrap package made from a single sheet, the package may be opened by peeling of the top seal and then tearing along the side fold lines. The packages may include a first opening-stop located one side of the package and a second opening-stop located in the second side of the package. In a four side sealed package, the opening-stops may be in respective side seal zones. In a flow-wrap package, the opening-stops may be adjacent to the side fold lines of the package. The first and second opening-stops limiting opening of the first and second sides of the package.

In one aspect, a package for containing a medical device wherein the package includes a front sheet and a back sheet and each of the front sheet and back sheet includes an inner surface facing the other sheet, an outer surface facing the ambient atmosphere, a top edge, a bottom edge and opposed first and second side edges. The front sheet and back sheet being sealed to each other by a peelable peripheral seal so that a cavity for containing a medical device is defined between the front sheet and the back sheet. The peripheral seal having a top seal zone, bottom seal zone, and opposed first and second side seal zones wherein the first side seal zone of the peripheral seal extends along at least a portion of the first side edges of the front and back sheets and the second side seal zone of the peripheral seal extends along the second side edges of the front and back sheets. The front and back sheets being separated to open the package by at least partially peeling the sheets apart along the opposed first and second side seal zones of the peripheral seal. The peripheral seal including a first peel-stop located in the first side seal zone of the peripheral seal and a second peel-stop located in the second side seal zone of the peripheral seal. The first and second peel-stops limiting peeling of the first and second side seal zones of the peripheral seal.

In another aspect, a package for containing a medical device wherein the package includes a rectangular body having a top edge, bottom edge and opposed side edges. The rectangular body also has a front wall formed of a flexible material. The package also includes a tear initiator associated with the body of the package wherein the tear initiator is configured to initiate tearing of the package to form an opening.

In another aspect, a package for containing a medical device wherein the package includes a body having a front wall formed of a flexible material and a slit in the front wall of the body that defines a flap opening. The package also includes a rim extending at least partially along the slit and projecting from an interior surface of the front wall.

In yet another aspect, a package for containing a medical device wherein the package includes a tray defining a cavity for holding a medical device. The package also includes a flexible sheet sealed to the tray and at least one projection projecting upward from the interior surface of the tray wherein the projections are configured to impede the flow of liquid.

In another aspect, a package for containing a medical device wherein the package includes a tray defining a cavity for holding a medical device and a flexible sheet sealed to the tray. The package also includes at least one well formed in the tray wherein the at least one well is configured to contain a liquid.

In another aspect, a package for containing a medical device wherein the package includes a pouch formed from a flexible material and a rigid ring-shaped opening wherein the flexible pouch is attached to the rigid ring-shaped opening.

In a further aspect, a package for containing a medical device wherein the package includes a body formed from a flexible material and a fin seal extending the length of the body. The package also includes a tear initiation line in the fin seal and a pull tab attached to the fin seal.

In yet another embodiment, a package for containing a medical device wherein the package includes a cavity for containing a medical device and a hydration liquid. The package also including a plurality of pockets within the cavity for containing the hydration liquid when the package is opened.

In another aspect, a method of packaging a catheter includes placing a hydrophilic catheter and a hydrating liquid in a first compartment of a package. A vapor donating medium is placed in a second compartment of the package wherein the first and second compartments are separated by a liquid impermeable, vapor permeable material.

BRIEF DESCRIPTION OF DRAWINGS

FIG. 1 is a top plan view of one embodiment of a medical device package in accordance with the present disclosure;

FIG. 2 is a perspective view of the package of FIG. 1 shown in a partially open configuration;

FIG. 3 is a top plan view of the package of FIG. 1 shown in a partially open configuration;

FIG. 4a is a top perspective view of another embodiment of a medical device package in accordance with the present disclosure;

FIG. 4b is a front plan view of another embodiment a medical device package in accordance with the present disclosure;

FIG. 4c is a back plan view of the package shown in FIG. 4b;

FIG. 4d is an elevated side view of the package shown in FIG. 4b;

FIG. 5 is a plan view of another embodiment of a medical device package in accordance with the present disclosure;

FIG. 6 is a plan view of another embodiment of a medical device package in accordance with the present disclosure;

FIG. 10 is a perspective view of another embodiment of a medical device package in accordance with the present disclosure;

FIG. 11 is a perspective view of the medical device package of FIG. 10 shown with the tear initiation element initiating tearing of the package material to define an opening in the package;

FIG. 16 is a perspective view of another embodiment of a medical device package in accordance with the present disclosure;

FIG. 17 is a perspective view of another embodiment of a medical device package in accordance with the present disclosure;

FIG. 20 is a perspective view of another embodiment of a medical device package in accordance with the present disclosure;

FIG. 21 is a perspective view of the medical device package of FIG. 20 shown with a catheter stored within the package;

FIG. 24 is a plan view of another embodiment of a medical device package in accordance with the present disclosure;

FIG. 25 is a plan view of the medical device package of FIG. 24 shown with the tear initiation element and directional tear element defining an opening of the package;

DETAILED DESCRIPTION OF THE EMBODIMENTS

Figure 7:
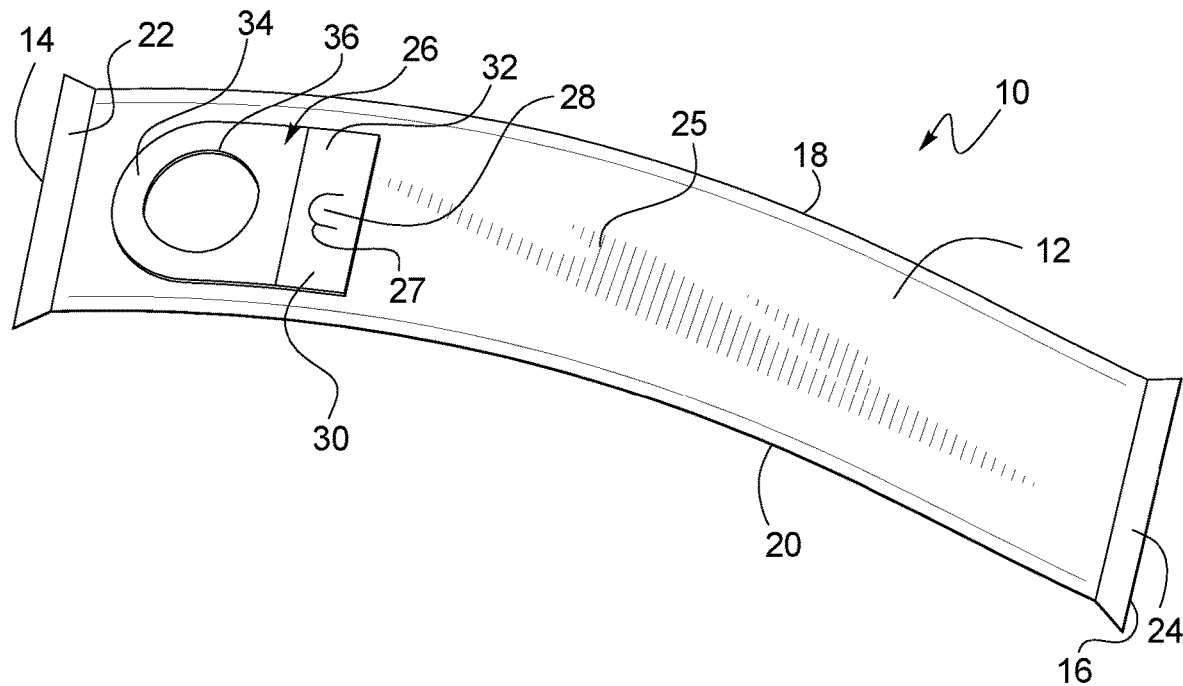
FIG. 7 is a perspective view of another embodiment of a medical device package in accordance with the present disclosure.

The present disclosure is generally directed to medical device packages which may be particularly, but not exclusively, useful in the packaging of medical devices and a fluid. For example, the medical device packaging may be useful in the packaging of a hydrophilic medical device and a hydration liquid for hydrating the hydrophilic medical device. In one particular application, the packages of the present disclosure include a hydrophilically coated urinary catheter and a hydration liquid that is loose within the package. The hydration liquid may be initially loose within the package or may become loose within the package, e.g., released from a sachet by the end user. The packages disclosed herein may include features/elements that assist in reducing the risk of liquid spillage when user opens the package and removes that medical device from the package for use.

While the packages of the present disclosure may be described herein relative to urinary catheters, the packages are not limited to such use and may be used with any suitable medical device. For example, the packages may be used with endoscopes, drainage catheters, vascular catheters, vaginal and fallopian tube devices, etc.

FIGS. 1-4a and 4b-4d, illustrate top peel open packages wherein the packages are initially opened along the top and then along the sides of the package. FIGS. 1-3 illustrate a four side sealed package that includes two sheets sealed together. This package may be opened by peeling apart the two sheets at the top seal and then peeling along the side seals. FIGS. 4b-4c illustrated a flow-wrap package made from a single sheet having a fin seal and two end seals wherein the sides of the package a defined by fold lines. This package may be opened by peeling of the top seal and then tearing along the side fold lines. Each of these packages may include a first opening-stop located in the first side of the package and a second opening-stop located in the second side of the package. In a four side sealed package, the opening-stops may be located in the respective side seal zones. In a flow-wrap package, the opening-stops may be located adjacent to the respective side fold lines of the package. The first and second opening-stops limiting opening of the first and second sides of the package.

FIGS. 1-3 illustrate a medical device package 10a for containing a medical device 12a. The package 10a includes a front sheet 14a and a back sheet 15a (FIGS. 2 and 3). The front sheet 14a includes an inner surface 16a facing the back sheet 15a, an outer surface 17a facing the ambient atmosphere, a top edge 18a, bottom edge 19a and opposed first and second side edges 20a and 21a. Referring to FIGS. 2 and 3, the back sheet 15a includes an inner surface 22a facing the front sheet 14a, an outer surface (not shown) facing the ambient atmosphere, a top edge 23a, bottom edge (not shown) and opposed first and second side edges 24a and 25a.

The front sheet 14a and back sheet 15a may be made from a liquid and gas impermeable material. For example, the front and back sheets 14a and 15a may be made from a polymer film and/or a metal film. In one embodiment, the material may be a polymer/metal laminate, such as a polymer/aluminum laminate.

The front sheet 14a and back sheet 15a may be sealed to each other to define a cavity for holding the medical device 36a. In one embodiment, the front sheet 14a and back sheet 15a may be sealed to each other to form a gas tight cavity. In the illustrated embodiment, the front sheet 14a and back sheet 15a are sealed to each other by a peripheral seal 26a. The peripheral seal 26a may be a peelable seal that may be a heat seal, an adhesive seal or any other suitable peelable seal that allows the front sheet 14a to be separated from the back sheet 15a when the sheets are peeled apart during use.

The peripheral seal 26a may include a top seal zone 27a, bottom seal zone 28a, and opposed first and second side seal zones 29a and 30a. The peripheral seal 26a is preferably a continuous seal. The first side seal zone 29a of the peripheral seal 26a may extend along at least a portion of the first side edges 20a and 24a of the front and back sheets 14a and 15a, and the second side seal zone 30a of the peripheral seal 26a may extend along the second side edges 21a and 25a of the front and back sheets 14a and 15a. The first and second side seal zones 29a and 30a may be at or spaced from the first and second side edges of the front and back sheets. The bottom seal zone 28a of the peripheral seal 26a may be at or spaced from the bottom edges of the front and back sheets 14a and 15a. The top seal zone 27a of the peripheral seal 26a may be spaced inwardly from the top edges 18a and 23a of the front and back sheets 14a and 15a such that the top edges 18a and 23a are free and not attached to each other. The top seal zone 27a may be in a linear configuration or non-liner configuration. For example, the top seal zone 27a may have a pointed shape, such as the chevron shape shown, or it may have a rounded chevron shape. Furthermore, the top sheet 14a and/or the bottom sheet 15a may, optionally, include a finger hole 33a to aid in grasping the sheets.

The package 10a also may include a first opening-stop, such as first peel-stop 31a, located in the first side seal zone 29a of the peripheral seal 26a. The package 10a also may include a second-opening-stop, such as second peel-stop 32a, located in the second side seal zone 30a of the peripheral seal 26a. The first and second peel-stops 31a and 32a limit peeling of the first and second side seal zones 29a and 30a of the peripheral seal 26a. In one embodiment, the first and second peel-stops 31a and 32a may prevent further peeling of the first and second side seal zones 29a and 30a of the peripheral seal. In another embodiment, the first and second peel-stops 31a and 32a may provide a tactile feel that alerts the user that the package has been sufficiently opened so that the user knows to stop peeling.

In use, the user opens the package 10a by grasping the front and back sheets 14a and 15a at or near the respective top edge 18a and 23a. The user may insert their finger through the finger hole 33a, if one is present. The user then pulls the front and back sheets 14a and 15a apart to initiate separation of the sheets. As the user pulls sheets 14a and 15a apart, the sheets peel apart at the top seal zone 27a of the peripheral seal 26a and then they peel apart along side seal zones 29a and 30a. As the user continues to pull the sheets 14a and 15a apart, the sheets peel apart along the side seal zones 29a and 30a until reaching the peel-stops 31a and 32a. When the peel-stops 31a and 32a are reached, further peeling may be prevented and/or the peel-stops may provide a tactile feel that alerts the user to stop peeling. As shown in FIG. 3, at that point, a selected segment of the medical device is exposed and the user may grasp the medical device and remove it from the package.

The first and second opening or peel-stops may have a variety of different configurations. For example, peel-stops 31a and 32a may be configured so that more force is required to peel the peel-stop portions of the peripheral seal 26a than other portions of the seal. In one embodiment, the first and second peel-stops 31a and 32a may comprise widened seal portions or seal portions of greater area than the adjacent portions, as shown in FIGS. 1 and 2. Optionally, the peel-stops 31a and 32a may include opening interruption elements, such as peel interrupt elements 34a and 35a. The peel interruption elements 34a and 35a may include cuts or perforations through the front sheet 14a and/or the back sheet 15a in the peel-stops 31a and 32a. The cuts or perforations may be die-cuts or laser-cuts and they may be any variety of shapes and sizes. For example, the peel interruption elements 34a and 35a may be generally J-shape, generally V-shape or generally hook-shape. Furthermore, the peel-stops 31a and 32a may be positioned so that the package opens to expose a selected portion of the medical device, such as the distal end of a catheter. In one embodiment, the peel-stops are positioned closer to the top seal zone of the peripheral seal than the bottom seal zone of the peripheral seal. In another embodiment, the peel-stops may be positioned such that only the distal end 36a of the medical device is exposed when the package is opened.

In the embodiments shown FIGS. 1-3, the package 10a is illustrated as containing a catheter as the medical device 12a. Also, the peel-stops 31a and 32a are positioned closer to the top seal zone 27a of the peripheral seal 26a so that when the package 10a is opened, the distal end 36a of the catheter is exposed. In another embodiment, the opening-stops or peel-stops may be positioned so that the distal third or less of the catheter is exposed. In the illustrated embodiment the catheter includes a gripping aid 36a' and the peel-stops may be positioned so that only the portion of the catheter that includes the gripping aid 36' may be exposed. The peel-stops 31a and 32a also include J-shaped peel interruption elements 34a and 35a. When the user peels the front and back sheets 14a and 15a along side seal zones 29a and 30a, the front and back sheets 14a and 15a peel apart along the side seal zones 29a and 30a until the peel-stops 31a and 32a are reached. When the peel-stops 31a and 32a are reached, the peel interruption elements 34a and 35a tear in the J-shaped pattern preventing further peeling along the side seal zones 29a and 30a, as shown in FIG. 3. Additionally, the tearing of peel interruption elements 34a and 35a may provide the user with a tactile feel to let the user know to stop peeling. If the user continues to peel the front and back sheets apart, the peel interruption elements 34a and 35a may direct the force toward the center of the sheets which will prevent further peeling or make the sheets harder to peel apart.

When the package 10a includes a liquid within the cavity, such as a hydration liquid, the peel-stops may also define pockets, wells, or indents 37a within the cavity (FIG. 1). When the package 10a is opened, the liquid may pool in the pockets 37a to prevent or reduce spillage. For example, when the package 10a includes a catheter and hydration liquid for hydrating a hydrophilic surface of the catheter, if the opened package is tilted, the liquid may pool or be collected in pockets 37a and be prevented from spilling out of the package. Furthermore, the front sheet 14a and/or the back sheet 15a may, optionally, include a channel 40a that extends lengthwise along the sheet. The channel 40a may be for collecting hydration liquid. When the front and back sheets are made from a polymer/metal laminate, the channels may be formed by pressing or stamping the sheets so as to have a desired shape, such as one or more channels. The sheets may also be formed to have indents or wells.

FIGS. 5 and 6 illustrate further embodiments of packages 250a and 250b which are four-sided sealed, top side peel open packages similar to that shown in FIG. 1. Packages 250a and 250b each include a front sheet and back sheet (not shown) that are sealed to each other by a peripheral seal 252a, 252b to define a cavity for containing a medical device, such as a catheter with a hydrophilic surface, and hydration liquid. The peripheral seal includes a top seal zone 254a, 254b, a bottom seal zone 256a, 256b, a first side seal zone 258a, 258b and a second side seal zone 260a, 260b. The top edges of the front and back sheets above the top seal zone 254a, 254b are unsealed so that the user may pull the top of the front and back sheets apart to peel open the top seal zone 254a, 254b, thereby initiating opening of the package. Optionally, the front and/or back sheets may include a finger hole 262a, 262b to assist the user in grasping the sheets.

The first side seal zone 258a, 258b and second side seal zone 260a, 260b may include a plurality of opposed wide seal portions or projections 262a, 262b that project into the cavity of the package and opposed narrow seal portions 264a, 264b. The wide seal portions 262a, 262b may be peel-stops. The wide and narrow seal portions 262a, 262b and 264a, 264b define pockets, wells, or indents 266a, 266b in the side seal zones within the cavity. When the packages 250a and 250b are opened, the liquid may pool in the pockets 266a, 266b to prevent or reduce spillage. For example, if the open package is tilted, the liquid may pool or be collected in pockets 266a, 266b and be prevented from spilling out of the package. In the illustrated embodiment, the wide seal portions or projections 262a, 262b may be at an angle to the rest of the side seal zones. The projections 262a, 262b also may define a V-shaped pocket with the narrow seal portions 264a, 264b. Furthermore, the projections 262a, 262b may also include peel interruptions elements, such as any of those described above. As illustrated in FIG. 6, the package may include more pockets by increasing the number of alternating wide and narrow seal portions.

Turning to FIG. 4a, there is shown another embodiment of a package 41a having a generally rectangular shape, which may be a square. Package 41a includes a front sheet and a back sheet (not shown) that are sealed to each other by a peripheral seal 42a to define a cavity for containing a medical device. The package may contain a catheter with a hydrophilic surface and hydration liquid. The peripheral seal 42a is a five side seal that includes a top seal zone 43a, upper seal zones 44a along two sides of the package and lower seal zones 45a along the other two sides of the package. The top seal zone is spaced from one of the corners 46a of the package 41a such that a portion 47a, 47a' of each of the front and back sheets are not attached to each other. The package 41a also includes peels-stops 48a which may be located anywhere along the upper seal zones 44a. In the illustrated embodiment, the peel-stops 48a are located between the upper seal zones 44a and the lower seal zones 45a. The peel-stops 48a may, optionally, include peel interruption elements 49a, such as any of the peel interruption elements described above.

To open the package 41a, the corner portions 47a, 47a' of the front and back sheets above the top seal zone 43a are peeled apart to unsealed the top seal zone 43a. The user continues to pull the front and back sheets apart to peel open side seal zones 44a until the peel-stops 48a are reached. The user then removes the medical device. In the embodiment, the medical device may be a catheter or other device that is coiled or otherwise folded to fit in the package.

Turning to FIGS. 4b-4c, there is shown another embodiment of a medical device package 10b. Package 10b is a flow-wrap package made from a single sheet of material. Package 10b is formed by folding the single sheet at fold line 16b and fold line 18b. The sheet is then sealed at or near the top edge 20b of the sheet by a top seal 22b. The sheet is sealed at or near the bottom edge 24b by a bottom seal 25b. The side edges of the sheet are also sealed at a fin seal 28b (FIG. 4b). The formed package 10a includes a front panel 12b (FIG. 4b) and a rear panel 14b (FIG. 4c) defined between fold lines 16b and 18b. The fold lines 16b and 18b define the side edges of the package. The fold lines 16*b* and 18*b* may be cut above the top seal 22*b* so as to define two flaps 30*b* and 32*b*. Flaps 30*b* and 32*b* may be grasped by the user and pulled apart to peel open the top seal 22*b* and to tear the package along fold lines 16*b* and 18*b*.

The package 10*b* also may include a first opening-stop 34*b* and a second opening-stop 36*b*, wherein each opening-stop is located at or near a respective side edge 16*b* and 18*b* of the package 10*b*. The opening-stops also may be at or adjacent to the top seal. The first and second opening-stops 34*b* and 36*b* limit tearing of the package along the side edges of the package defined by fold lines 16*b* and 36*b*. In one embodiment, the first opening-stop 34*b* and second opening-stop 36*b* may prevent further tearing of the first and second side edges of the package. In another embodiment, the first opening-stop 34*b* and second opening-stop 36*b* may provide a tactile feel that alerts the user that the package has been sufficiently opened so that the user knows to stop tearing the package. The first opening-stop 34*b* and second opening-stop 36*b* may be any of those described above. For example, the first opening-stop 34*b* and second opening-stop 36*b* maybe a sealed portion wherein a portion of the front panel 12*b* and back panel 14*b* are sealed together. Optionally, the first opening-stop 34*b* and second opening-stop 36*b* may include opening interruption elements 38*b*, such as J-shaped, generally V-shaped or generally hook-shape cuts or perforations, as described above.

In use, the user opens the package 10*b* by grasping flaps 30*b* and 32*b*. The user may insert their finger through the finger hole, if one is present. The user then pulls the flaps 30*b* and 32*b* apart to separate top seal 22*b*. As the user continues to pulls flaps 30*b* and 32*b* apart, the package tears along the side edges defined by fold lines 16*b* and 18*b* until reaching the opening-stops 34*b* and 36*b*. When the opening-stops 34*b* and 36*b* are reached, further opening may be prevented and/or the opening-stops may provide a tactile feel that alerts the user to stop opening the package.

FIGS. 7-9*c* illustrate a medical device package 10 of the present disclosure. Package 10 may be a flow-wrap package, four-sided sealed package formed from front and back sheets, or any other suitable package that is formed from a multilayered laminate film. When package 10 is a four-sided sealed package, it may be a cold-form package wherein one of the sheets is pressed or stamped so as to have a desired shape, such as one or more channels, indents or wells. In the illustrated embodiment, package 10 includes an elongated body 12 having a top edge 14, a bottom edge 16 and opposed side edges 18 and 20. Package 10 includes a seal 22 at or near top edge 14 and a seal 24 at or near bottom edge 16. In the illustrated embodiment, package 10 is substantially rectangular wherein the lengths of the opposed sides are greater than the lengths of the top and bottom. In other embodiments, the lengths of the sides may be the same as the lengths of the top and bottom.

When package 10 is a four-sided sealed package, the front sheet and back sheet (not shown) forming the package may be sealed to each other about their peripheries to define an inner cavity that holds the medical device and, optionally, a hydration liquid. For example, package 10 may include a continuous four-sided peripheral seal that extends along the top edge 14, side edges 18 and 20 and bottom edge 16. When package 10 is a flow-wrap package, the body 12 of the package may be generally tubular and include the top seal 22, bottom seal 24 and a fin seal (not shown) at the rear of the body 12. Furthermore, the side edges 18 and 20 may be formed or defined by folds of the flow-wrap package.

The material from which package 10 is formed may be a multilayered flexible laminate film(s). Such films may include a weldable inner layer and a protective middle or outer layer. For example, the laminate films may include a polymeric inner layer, a metallic middle layer and a polymeric outer layer. The multilayered laminate film may also include a directional tear element that directs the film to tear in a desired direction. In one example, the directional tear element may direct the laminate film to tear in a substantially linear manner. In one embodiment, the directional tear element may be a controlled directional tear laminate film that may include one or more layers of oriented polymer which controls the direction or the tearing of the film. For example, the controlled directional tear film may direct the film to tear in a substantially linear line. In another embodiment, the directional tear element may be a directional tear tape that is superimposed over at least a portion of the film and directs the film to tear in a desired direction.

Package 10 may also include a tear initiator or tear initiation element 26 associated with a front wall 25 of the body 12. In the illustrated embodiment, the tear initiator 26 includes a tear initiation line 27, such as a slit or perforation in the package material. The tear initiation line 27 may form a tear initiation flap or tongue 28 in the laminate film. The tear initiator tab 28 may be located spaced from the top seal 14 and is preferably positioned between opposed sided edges 18 and 20. In the illustrated embodiment, the tear initiator tab 28 is centered between the opposed side edges, but it may also be closer to one side edge or the other. The tear initiator 26 also includes a gripping portion 30 that the users grips and pulls to initiate tearing of the package material to form an opening in the package. In the illustrated embodiment, the gripping portion is shown as a pull tab 30 that has an adhesive portion 32 which is attached to the body 12 of the package 10 and an unattached portion, such a free end 34. The adhesive portion 32 is adhered to the package and overlies the tear initiation flap 28. In the illustrated embodiment, the free portion 34 includes a generally rounded shape and defines a finger hole 36 therethrough. In other embodiments, the free portion 34 may be any other suitable shape and may or may not include a finger hole. In use, the user may grasp and pull the free portion 34 of the pull tab 30 to initiate tearing of the package material to form an opening in the front wall 25 of the body 12.

Figure 8:
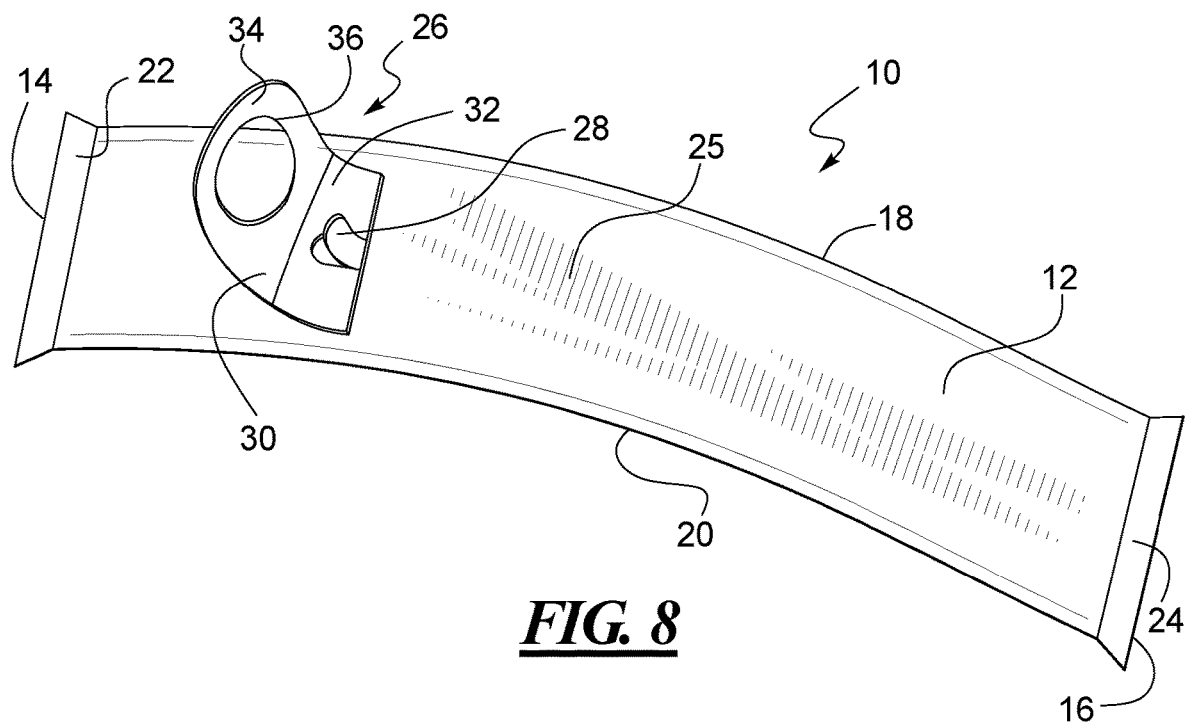
FIG. 8 is perspective view of the medical device package of FIG. 7 shown with the tear initiation element initiating tearing of the package material to define an opening in the package.
Figure 9A:
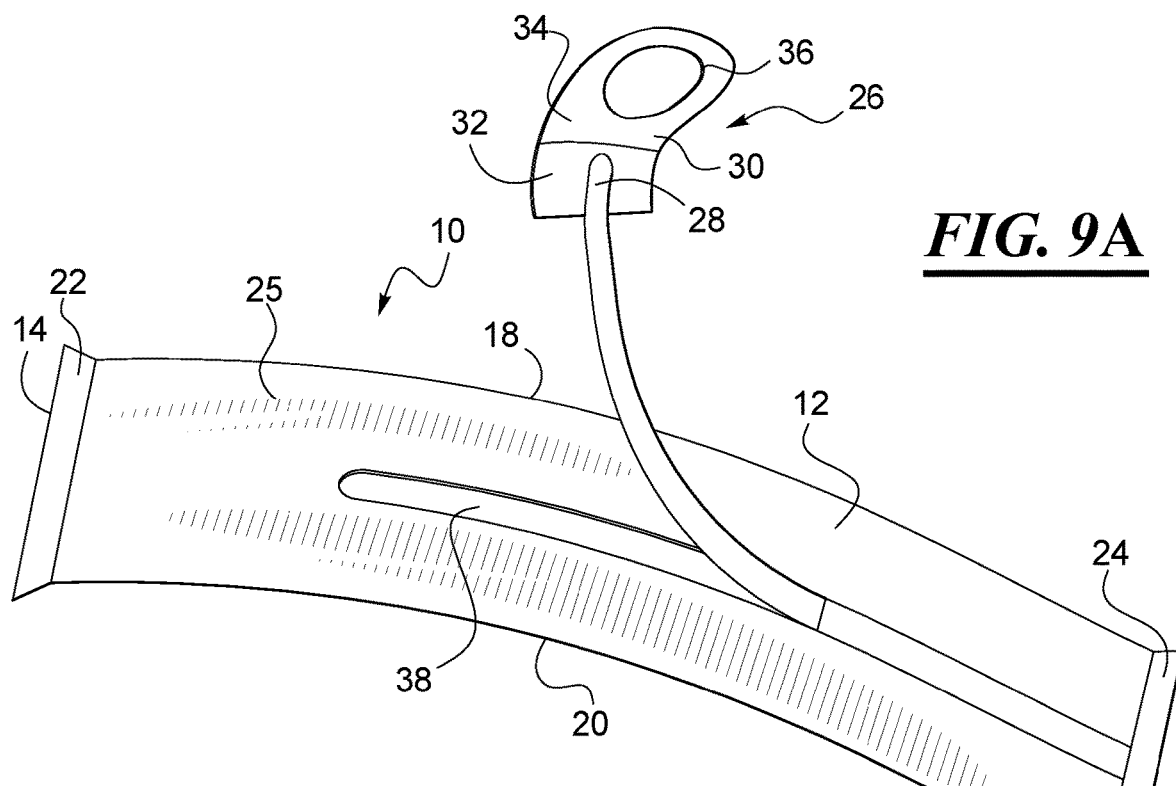
FIG. 9A is perspective view of the medical device package of FIG. 7 showing the package in a partially opened configuration.

Referring to FIGS. 8 and 9A, to open package 10, the user grasps the free end 34 of the pull tab 30 and pulls. As the pull tab 30 is pulled, the adhesive portion 32 of the pull tab 30 remains adhered to the tear initiation flap 28, but releases from the package material surrounding the flap 28. As the user continues to pull the pull tab 30, the tear initiation flap 28 initiates longitudinal tearing of the front wall 25 of the body 12 of the package 10, thereby forming a longitudinal opening 38 that is parallel or substantially parallel to the one or both of the side edges 18 and 20 and extends from the initial location of the tear initiation flap 28 toward the bottom edge 16 of the body 12 of the package 10. In one embodiment, the package includes a directional tear element that directs the package material to form a substantially linear tear. The user may pull the pull tab 30 until a desired sized opening 38 is created in the front wall 25 of the package. Additionally, the bottom seal 24 may serve as a stop that stops the tearing of the material of the package.

Figure 9B:
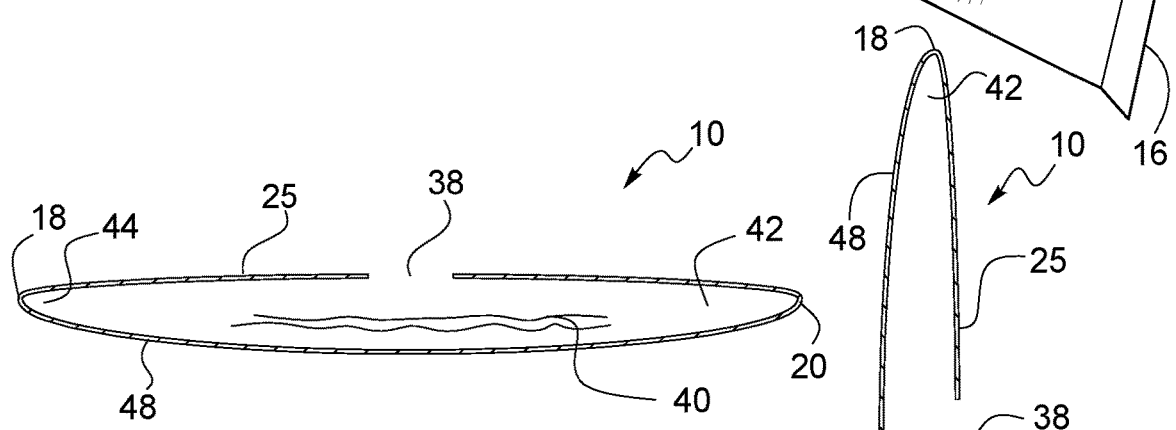
FIG. 9B is a cross-sectional view of the medical device package of 9A.
Figure 9C:
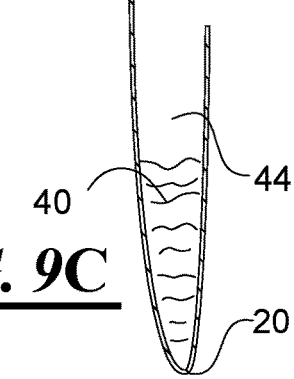
FIG. 9C is a cross-sectional view of the medical device package of 9A shown with the package being turned to one side.

Once the desired opening 38 is formed, the user may reach into the package through opening 38 to remove the catheter. As shown in FIGS. 9B and 9C, the inner cavity of the package defines a space for containing fluid 40 within the package 10 and the narrow, longitudinal opening 38 reduces the risk of accidental spilling of the fluid 40 from the package 10. Additionally, opposed side pocket-like areas 42 and 44 are defined between the opening 38 and the front wall 25 and back wall 48 of package 10 wherein the fluid 40 may flow and collect in such pocket areas 42 and 44 when the package is turned to one side or the other, as illustrated in FIG. 9C. The ability for the fluid 40 to pool in the pocket areas 42 and 44 also assist in reducing accidental spillage of the fluid when the package 10 is turned to one side or the other.

Figure 12:
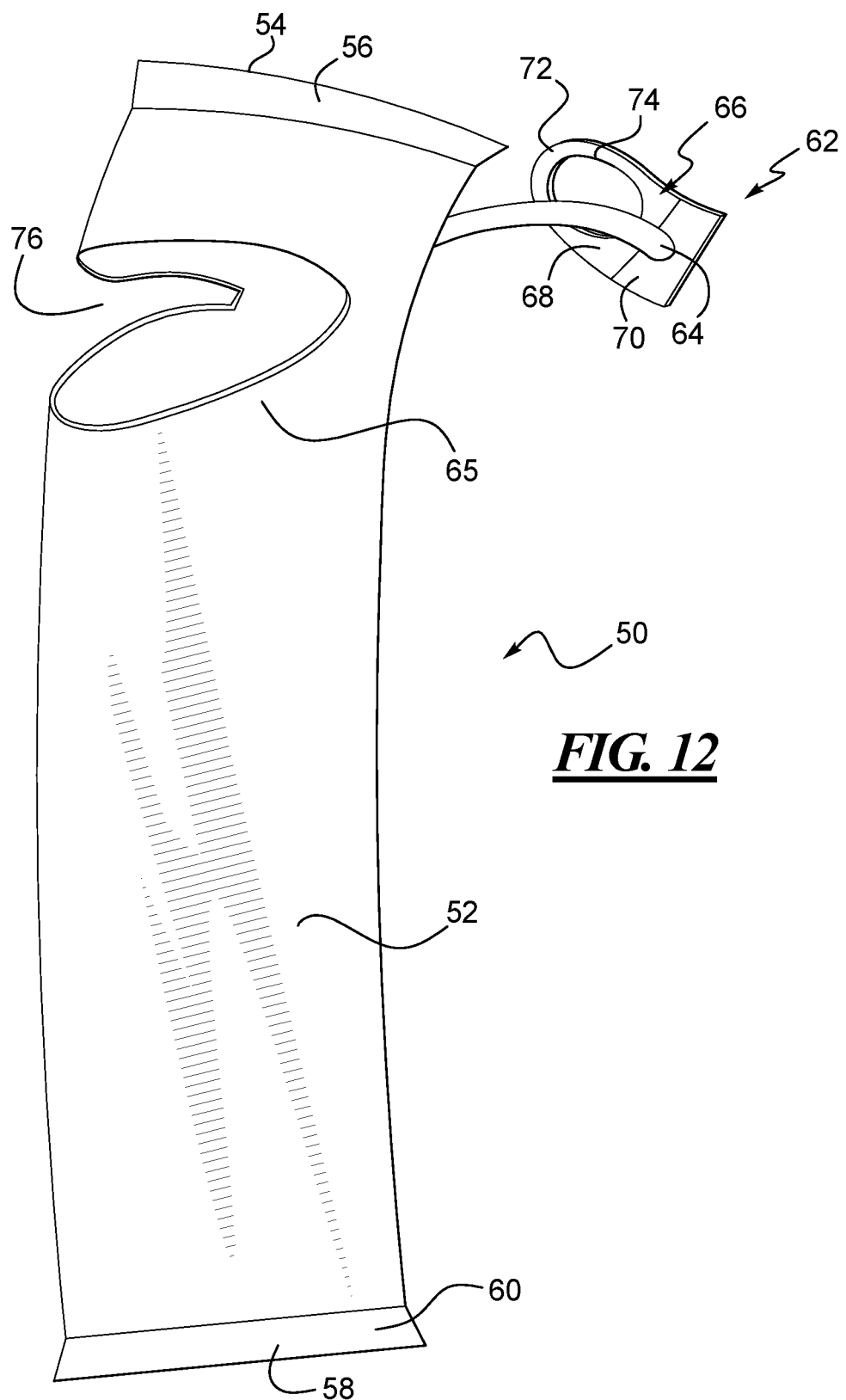
FIG. 12 is a perspective view of the medical device package of FIG. 10 showing the package in partially opened configuration.

FIGS. 10-12 illustrate another embodiment of a package 50 in accordance with the present disclosure. In this embodiment, the package 50 is configured to tear circumferentially to create an opening for removing the medical product. In the illustrated embodiment, package 50 includes an elongated body 52 having a top 54 and a seal 56 at or near 54. The package 50 also includes a bottom 58 and a seal 60 at or near the bottom 58.

Similar to the previous embodiment, the material from which the package 50 may be made may be a multilayered laminate film. Furthermore, package 50 may include a directional tear element, such as a controlled directional tear film, scoring of the laminate film (e.g., laser scoring) or a tear tape. Package 50 may also include a tear initiator or tear initiation element 62. In the illustrated embodiment, the tear initiator 62 includes tear initiation line 63, such as a slit or perforation in the package material. The tear initiation line 63 may form the illustrated tear initiation flap or tongue 64. The tear initiation flap 64 may be located at any location along the body 52 of package 50, depending on the desired application. In the illustrated embodiment, the tear initiation flap 64 is adjacent to and spaced from the top seal 56. However, in other embodiments it may be adjacent to and spaced from the bottom seal 60 or in the middle of body 52 of package 50. The tear initiator 62 also includes a gripping portion 66 that the users grips and pulls to initiate tearing of the package material to form an opening in package 50. In the illustrated embodiment, the gripping portion includes a pull tab 68 that has an adhesive portion 70 which is attached to the front wall 65 of the body 52 of the package 50 and an unattached portion, such a free end or portion 72. The adhesive portion 70 is adhered to the package 50 and overlies the tear initiation flap 64. In the illustrated embodiment, the free portion 72 includes a generally rounded shape and defines a finger hole 74 therethrough. In other embodiments, the free portion 72 may be any other suitable shape and may or may not have a finger hole. In use, the user may grasp and pull the free portion 72 to initiate tearing of the package material to form an opening.

Referring to FIGS. 11 and 12, to open package 50, the user may hold the package in an upright position and then grasp the free end 72 of the pull tab 68 and pull. As the user pulls the pull tab 68, the adhesive portion 70 remains adhered to the tear initiation flap 64, but releases from the package material surrounding the flap 64. As the user continues to pull on pull tab 68, the tear initiator flap 64 initiates a circumferential tear in the body 52 of the package 50 that forms opening 76 that extends at least partially circumferentially about package 50. The user may pull the pull tab 68 until a desired sized opening is created within package 50. With package 50 in the upright position, any fluid within package 50 may pool towards the bottom 58 of the package to prevent spillage. Once the desired opening 76 is formed, the user may reach into the package 50 through the opening 76 to remove the medical device, such as a catheter, from the package.

Figure 13:
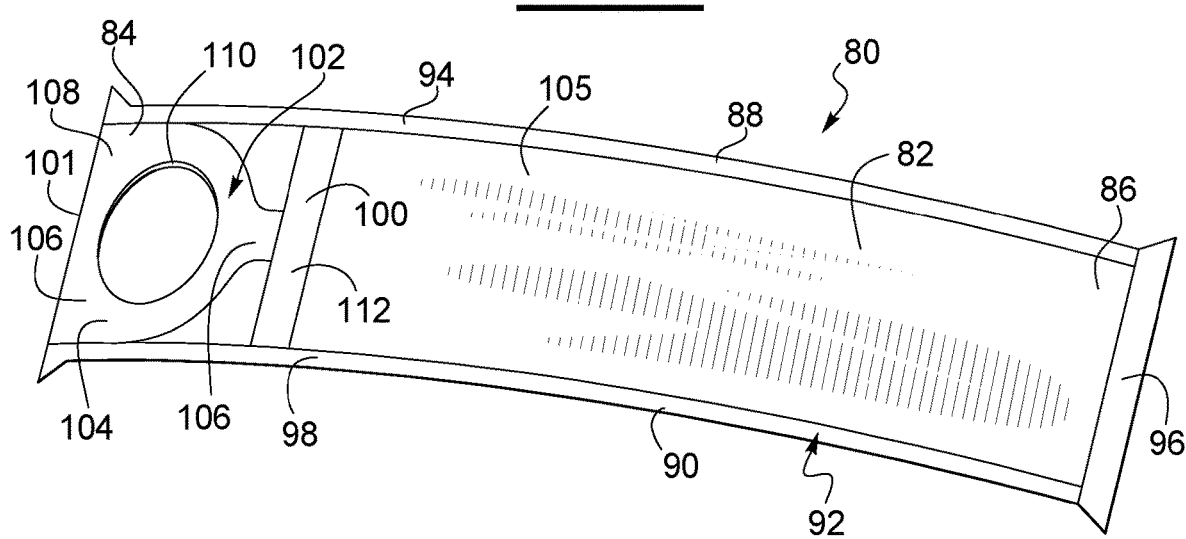
FIG. 13 is a perspective view of another embodiment of a medical device package in accordance with the present disclosure.
Figure 14:
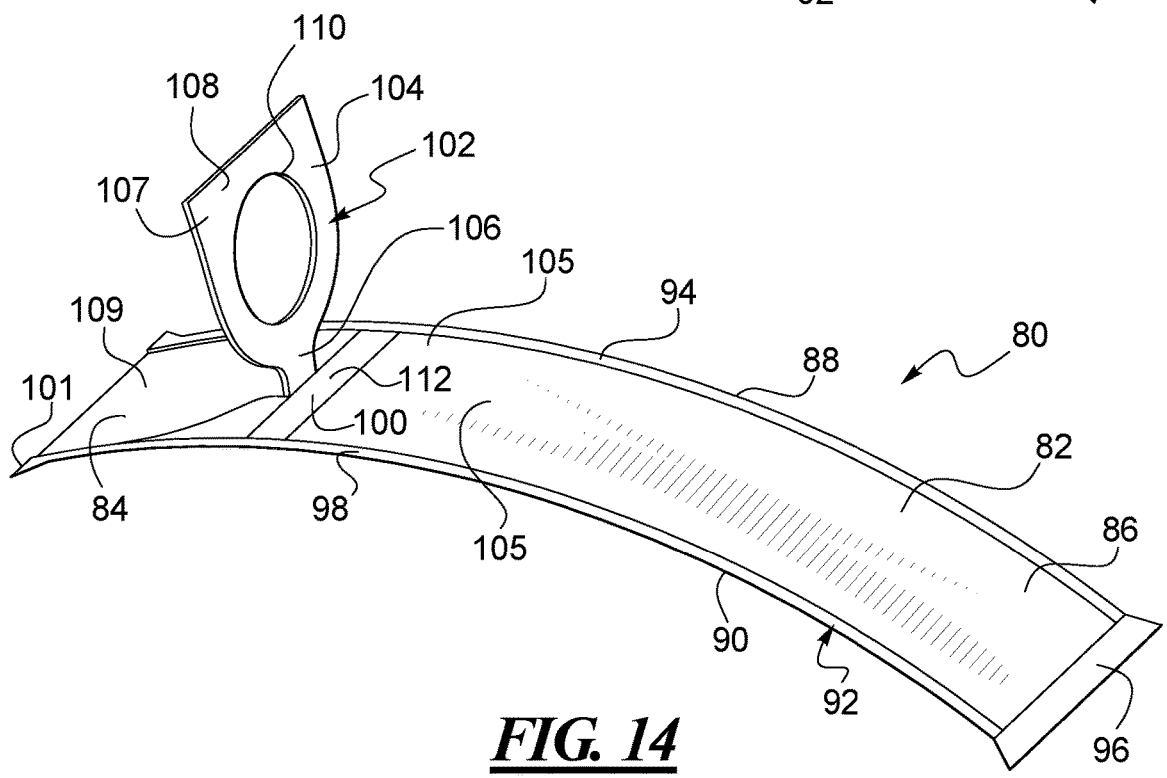
FIG. 14 is a perspective view of the medical device package of FIG. 13 shown with the tear initiation element initiating tearing of the package material to define an opening in the package.
Figure 15:
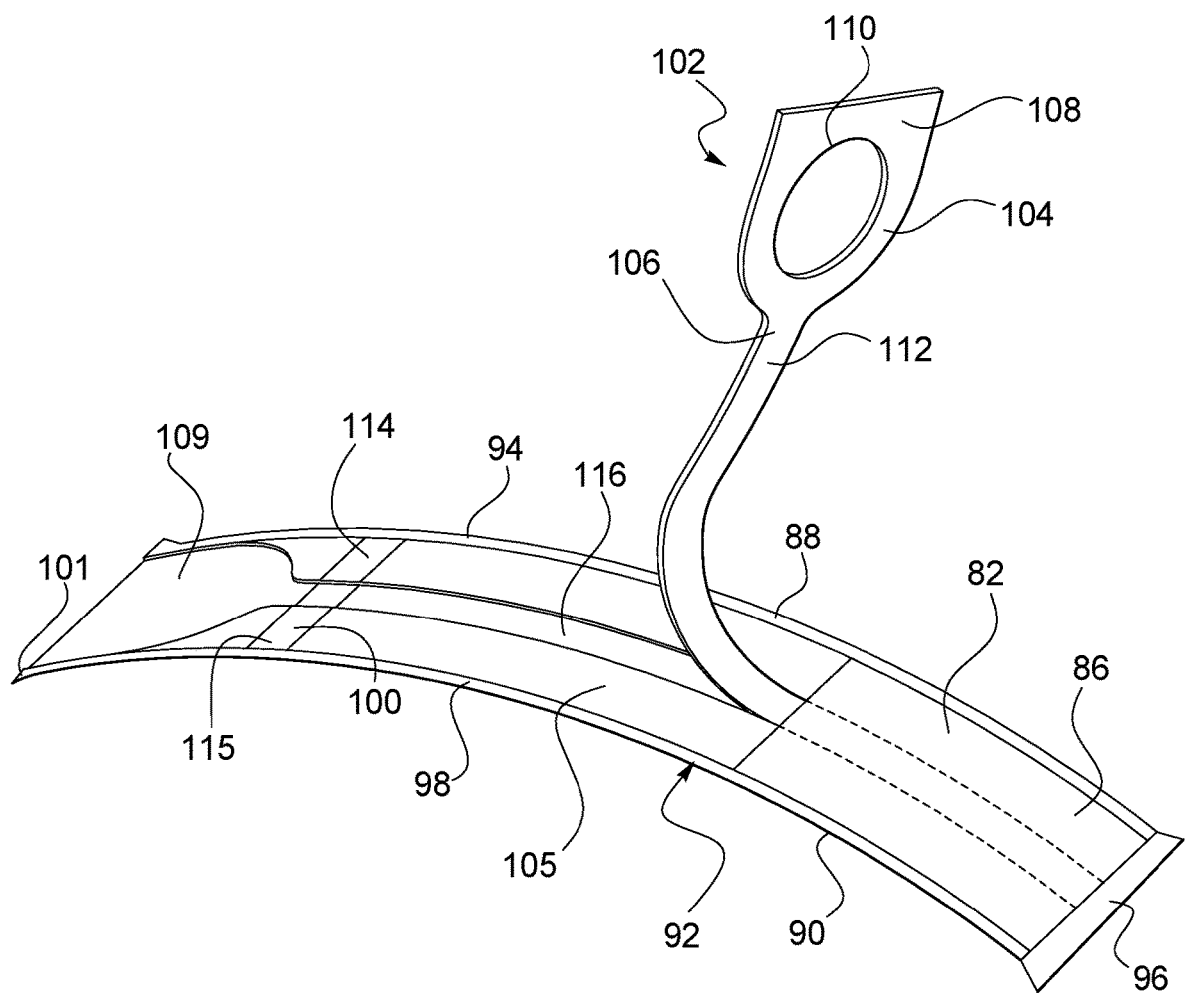
FIG. 15 is a perspective view of the medical device package of FIG. 13 showing the package in a partially opened configuration.

FIGS. 13-15 illustrate another embodiment of a medical device package in accordance with the present disclosure. Package 80 includes an elongated body 82 having a top portion 84, a bottom portion 86 and opposed sides 88 and 90. Package 80 may be made from front and back sheets that are sealed to each other to define an inner cavity that holds the medical device and, optionally, a fluid. In the illustrated embodiment, package 80 includes a continuous four-sided seal 92 that includes a longitudinal side segment 94 that extends along the side 88, a bottom transverse segment 96 that extends along the bottom portion 86, a longitudinal side segment 98 that extends along the side 90 and a top transverse segment 100 that extends across the package at a location spaced from the top edges 101 of the front and back sheets. In the illustrated embodiment, the longitudinal segments 94 and 98, which extend along the sides 88 and 90 of the package 80, also extend upwardly past the top transverse segment 100.

Package 80 also includes a tear initiator or tear initiation element 102. Tear initiator 102 may be a pull tab 104 formed in the front wall 105 of the package 80. The pull tab may be formed by or cut from a top portion 107 of the front sheet. For example, the pull tab 104 may be formed by a kiss cut that cuts the top sheet to form the pull tab 104 without cutting the rear sheet 109. In the illustrated embodiment, the pull tab 104 may be formed by a kiss cut in the top sheet between the segments 98 and 94 of the seal 92 and above the top transverse segment 100 of the seal 92. The pull tab 104 includes a stem 106 and a free portion 108. The stem 106 is attached to the body 82 of the package 80 at the top seal segment 100. The stem 106 preferably has a width that is shorter than the top transverse seal segment 100. In the illustrated embodiment, the stem 106 is attached at the center of the top transverse seal segment 100. However, the stem 106 be attached at other portions of the top transverse seal segment 100. The free portion 108 of the pull tab 104 is not attached to the rear sheet 109 such that the user may grasp and separated it from the rear sheet 109. In the illustrated embodiment, the free portion 108 includes a generally rounded shape and defines a finger hole 110 therethrough. In other embodiments, the free portion 108 may be any other suitable shape and may or may not have a finger hole. In use, the user may grasp and pull the free portion 108 to initiate tearing of the package material to form an opening.

Referring to FIGS. 14 and 15, to open the package, the user grasps the free portion 108 of the pull tab 104 and pulls. As the pull tab 104 is pulled, the stem 106 initiates tearing of a narrow portion 112 of the package material through the top transverse seal segment 100. The narrow portion 112 is a portion that is aligned with and attached to stem portion 106. The portions of the packaging material 114 and 115 (FIG. 15) located in the transverse seal segment 100 and on either side of the narrow portion 112 remain sealed/attached to the rear sheet. As the user continues to pull the pull tab 104, the package material continues to tear in a substantially linear manner toward the bottom 86 of the package 80 to form a longitudinal opening 116 that is parallel or substantially parallel to the one or both of the sides 88 and 90. The user may pull the pull tab 104 until a desired sized opening is created within the package. Additionally, the bottom transverse seal segment 96 may serve as a stop to stop the tearing of the material of the package.

Once the desired opening 116 is formed, the user may reach into the package through the opening to remove the catheter. Similar to that shown in FIGS. 9B and 9C, the inner cavity of the package 80 defines a space for containing fluid within the package and the narrow opening 116 reduces the risk of accidental spilling of the fluid from the package. Additionally, opposed side pocket-like areas are defined between the opening 116 and the front and back of the package wherein the fluid may flow and collect to assist in reducing the risk of spillage.

FIG. 16 illustrates another embodiment of a package 120 in accordance with the present disclosure. Package 120 may be a flow-wrap package, four-sided sealed package formed from front and back sheets, or any other suitable package that is formed from a multilayered laminate film. When package 120 is a four-sided sealed package, it may be a cold-form package wherein one of the sheets is pressed or stamped so as to have a desired shape, such as one or more channels, indents or wells.

The front wall 128 of the package 120 may include a slit 122 defining a flap opening 124. In one embodiment, the slit 122 may be a perforated line. A sheet 126 is attached to the front wall 128 of the package 120. The sheet 126 has an adhesive portion 130 that is attached to the front wall 128 of the package 120 and overlies the flap opening 124 and the slit 122. The sheet 126 also includes a free end 132 that is not adhered to the front 128 of the package 120. The free end 132 forms a gripping portion for peeling open the flap opening 124 the package 120. The package 120 also includes an internal rim 134 that projects from the inner surface 133 of the front wall 128 of the package 120 and extends at least partially along the periphery of slit 122 or edge of the front wall 128 that defines the opening in front wall 128 of the package 120 when the package is opened.

The rim 134 may be a separate component of the package 120 that is attached to the inner surface 133 of the front wall 128. For illustrative purposes, FIG. 16 shows the rim 134 outside of the package and being associated with an adhesive sheet 136. The arrows in FIG. 16 indicate where the adhesive sheet 136 and the rim 134 are attached to the inner surface 133 of the front wall of the package 120. In the illustrated embodiment the rim 134 is attached to an adhesive sheet 136 that extends outwardly from the rim 134. During the manufacturing of the package 120, the adhesive sheet 136 having the rim 134 attached thereto is adhered to the inner surface 133 of the front wall 128 of the package with the rim 134 aligned with the periphery of the slit 122 or edge of the front wall 128 that defines the opening. In another embodiment, rim 134 could be heat sealed to the inner surface 133 of the front wall 128, with or without the use of sheet 136.

In use, the free end 132 of the sheet 126 is grasped and the sheet 126 is peeled from the surface of the front wall 128, opening the opening flap 124 so that an opening is formed in the front wall 128 of the package 120. With the package 120 opened, the user may remove the medical device from the package 120 through the opening in the front wall 128. The rim 134 includes features that may assist in reducing accidental fluid spillage. For example, the rim 134 may act as a barrier that prevents fluid from escaping out of the opening of the package 120. Additionally, bending or flexing of the package material in the area of the opening may lead to accidental spillage. The rim 134 may provide strength or stiffness to this area of the package material so that the package material does not bend. The rim 134 also may contact the rear wall of the package so that the opening is spaced from the rear wall, which also may assist in preventing accidental spillage.

FIG. 17 illustrates another embodiment of a package 140 in accordance with the present disclosure. Package 140 includes a tray 142 and a sheet 144 that are sealed together at sides 146 and 148 and at top 150 and bottom 152. The tray 142 may be a multilayered laminate film including metal and polymer layers and that has been cold-formed to define a cavity 143 for holding a medical device. In another embodiment, the tray 142 may be a plastic tray. The sheet 144 may be a multilayered laminate film including metal and polymer layers. The sheet 144 may include a pull tab 154 for opening the package 140 by peeling the sheet 144 from the tray 142.

The tray 142 includes one or more projections 156 extending upward within the cavity 143 in the top portion 158 of the tray 142. The projections 156 may be formed by cold-forming a laminate film to include such projections. When the package 120 is opened, the projections 156 interrupt or impede the flow of fluid within the cavity, which assists in reducing the risk of accidental spillage.

Figure 18:
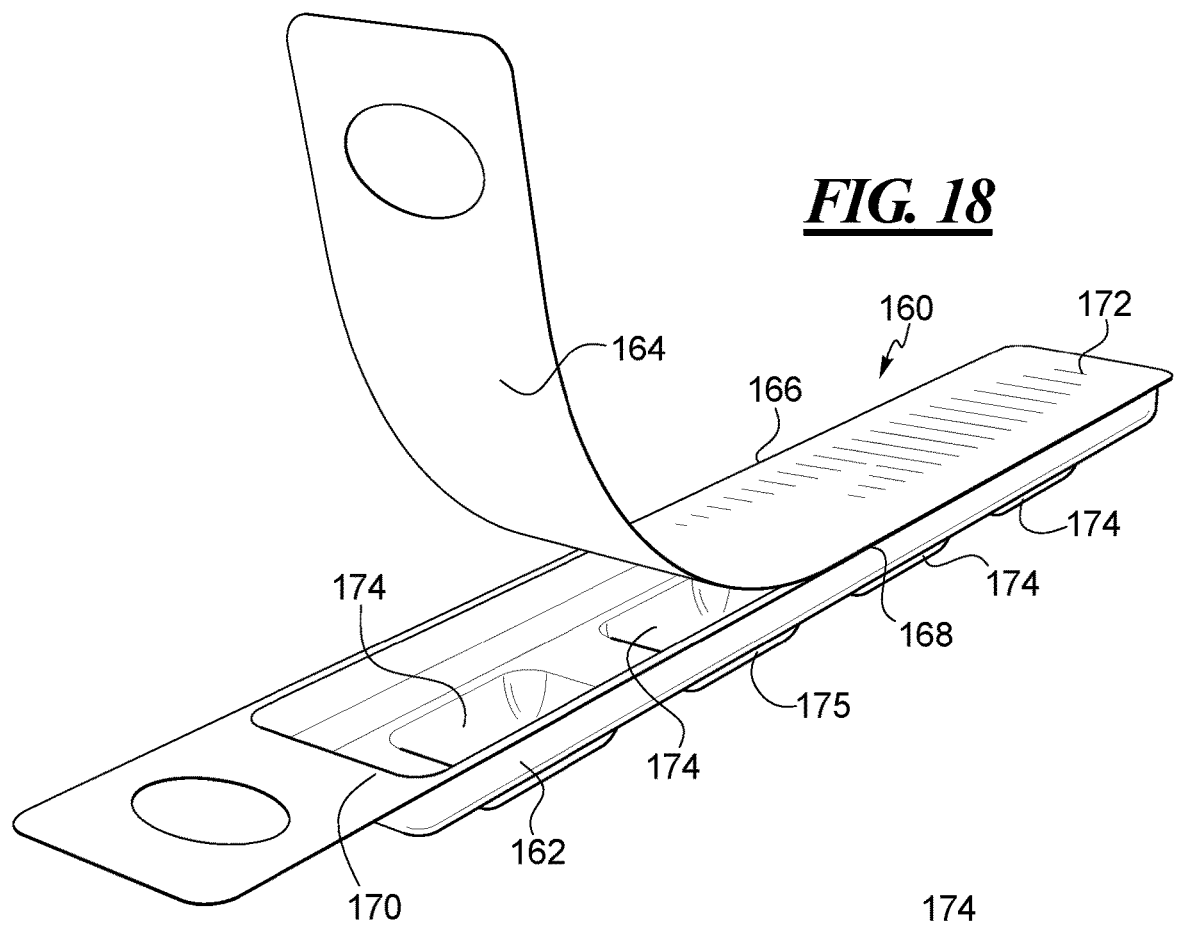
FIG. 18 is a perspective view of another embodiment of a medical device package in accordance with the present disclosure.
Figure 19:
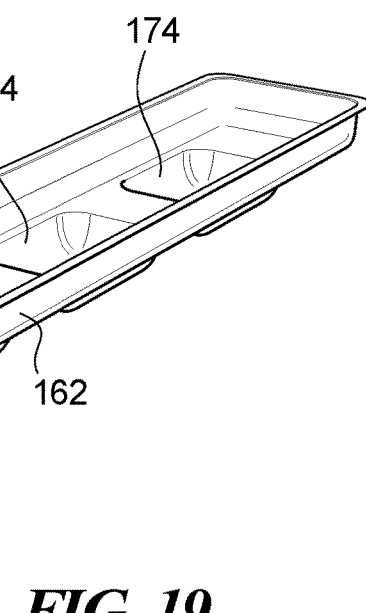
FIG. 19 is a perspective view of the bottom tray of the package shown in FIG. 18.

FIGS. 18 and 19 illustrate another embodiment of a package 160 in accordance with the present disclosure. Similar to package 150, package 160 includes a tray 162 and a sheet 164 that are sealed together along at sides 166 and 168 and at the top 170 and bottom 172. In this embodiment, the tray 162 includes one or more wells 174 for holding the fluid when the package 160 is place on the bottom surface 175 of the tray 162. The wells 174 may be formed by cold-forming of a laminate film. The wells 174 contain the fluid which aids in in reducing the risk of accidental spillage. Additionally, during manufacturing, the wells 174 may hold the fluid during packaging of the medical product. This may provide increase efficiency during manufacturing because the fluid is contained within the wells 174 and is not sloshing around during the forming of the packaged product.

FIGS. 20 and 21 illustrate another embodiment of a package 180 that includes a flexible body or pouch 182 that defines a cavity for containing a medical device and fluid. The package 180 also includes a spout or fitment 183. In the illustrated embodiment, the spout 183 includes a tube or ring 184 that defines a passageway 185 in communication with the cavity. The tube 184 includes a portion 187 that extends into the cavity such that a pocket-like space(s) 188 are defined between portion 187 of the tube 184 and the flexible body 182. The pocket-like space(s) 188 assist in preventing spillage in that the portion 187 of tube 184 prevents liquid from leaving the package and the liquid may gather in the pocket-like space(s) 188.

The flexible body 182 may be made from any of the multilayered flexible materials disclosed herein. The flexible body may be attached to the tube 184 by for example, adhesive or welding. Associated with the tube 184 is a removable cap 186 that covers the opening. The cap 186 may be connected to the tube 184 by threads, hinged, snap fit or the like. The fitment 183 could have different geometries for different device embodiments. For example, the fitment 183 may extend up out of the pouch wherein it may support a funnel of a catheter. In another embodiment, a urinary collection bag (not shown) may be wrapped around the fitment 183.

FIG. 21 shows a catheter 190 stored within the package 180 wherein the drainage end 192 of the catheter 190 projects from the tube 184. The user may remove the catheter 190 by grasping the drainage end 192. In one embodiment, the catheter 190 may include a retracted non-touch sleeve (not-shown) that is held in a collapsed state by the tube 184 wherein the sleeve covers the catheter shaft as the catheter 190 is removed from the package 180. In another embodiment the catheter may include a catheter gripper that may be positioned about the catheter shaft and sits on the outer portion 194 of the tube 184.

Figure 22:
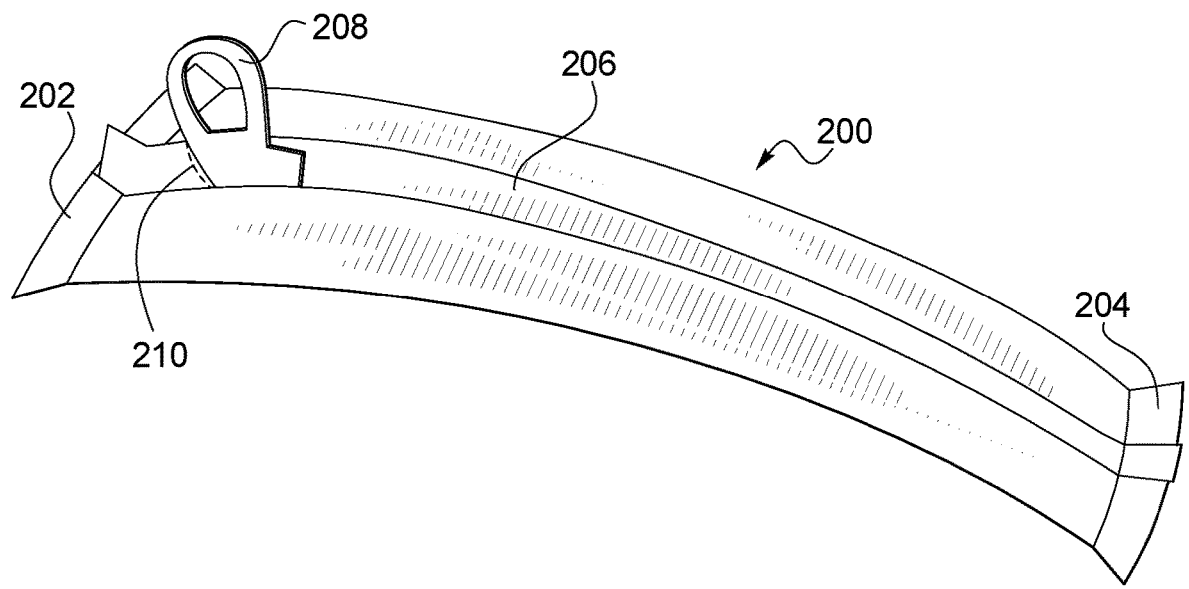
FIG. 22 is a perspective view of another embodiment of a medical device package in accordance with the present disclosure.
Figure 23:
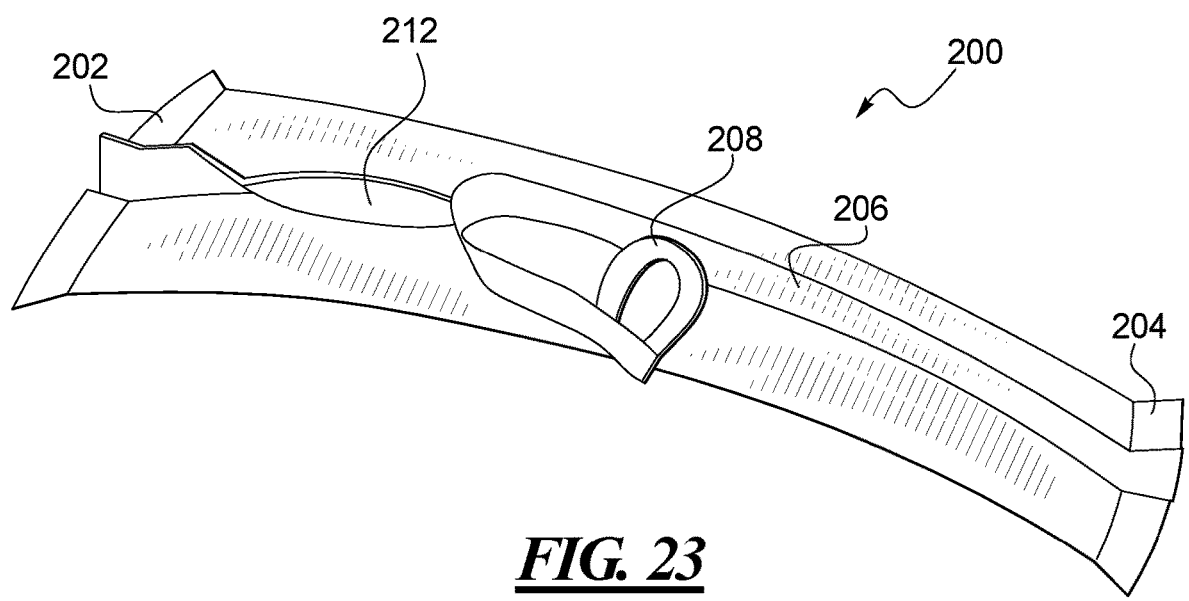
FIG. 23 is a perspective view of the medical device package of FIG. 22 shown with the tear initiation element initiating an opening of the package.

FIGS. 22 and 23 illustrate another embodiment of a package 200 in accordance with the present disclosure. The package 200 includes a top seal 202, a bottom seal 204 and a longitudinal fin seal 206 that extends the length of the package. A pull tab 208 is attached to the fin seal 206. In on embodiment the pull tab 208 is attached to the fin seal 206 adjacent to a tear starter line 210 that extends from the free edge of the fin seal 206 inward to facilitate the beginning of an opening tear. As shown in FIG. 23, when a user pulls the pull tab 208, the fin seal 206 tears along the starter line 210. As the user continues to tear the pull tab 208, the fin seal 206 tears from the package 200, thereby forming an opening 212 in the package.

FIGS. 24 and 25 illustrate another embodiment of a package 220. The package 220 may be a four-sided sealed package that has a front sheet and back sheet (not shown) that are sealed to each other by a peripheral seal 222 to form a cavity for containing a catheter and hydration liquid. In another embodiment, the package could be a single sheet that is folder over wherein the fold line defines one side of the package. The other three sides where the edges of the sheet meet are sealed together to form the top, bottom and other side seal. In another embodiment, the package could be a flow-wrap package. Turning back to FIGS. 24 and 25, the peripheral seal includes a top seal section 224, a bottom seal section 226, a first side seal section 228 and a second side seal section 230. The top seal section 224 may include a tear initiation line 234 that extends from the top edge 235 of the package through the top seal section 224 and a pull tab 236 for initiating tearing of the package along line 234. Optionally, the top seal section 224 may also include finger holes 238 and 240 that the user may grasp during opening of the package 220. The second side seal section 230 may include alternating wide seal portions or projections 242 that project into the cavity of the package and narrow seal portions 244. The wide and narrow seal portions 242 and 244 define pockets, wells, or indents 246 in the side seal section 230 within the cavity and pockets 249a, 249b at the top and bottom, respectively, of the cavity. The pocket 249a is defined by a wide seal portion 242 of the second side seal section 230, the top seal section 224 and the first side seal section 228. The pocket 249b is defined by a wide seal portion 242 of the second side seal section 230, the bottom seal section 226 and the first side seal section 228. When the package 220 is opened, the liquid may pool in the pockets 246, 249a, 249b to prevent or reduce spillage. For example, if the open package is tilted, the liquid may pool or be collected in pockets 246, 249a, 249b and be prevented from spilling out of the package. While the illustrated embodiment includes two pockets, the package may include more or less pockets by increasing the number of alternating wide and narrow seal sections.

The package 220 may include a directional tear element 248, such as a controlled directional tear film, scoring of the laminate film (e.g., laser scoring) or a tear tape, which extends through the wide seal portions 242 but is inside of the narrow seal portions 244. As shown in FIG. 25, the user may open the package 220 by pulling the pull tab 236 to initiate tearing along tear initiation line 234. As the user continues to pull on pull tab 236, the tear initiation line 234 leads the tearing of the package 220 to the directional tear element 248. The package 220 tears along direction tear element 248 to form an opening in the package for removing the catheter. Preferably, the catheter package is opened such that one or more pockets 246, 249a, 249b remain in the cavity of the package to collect liquid and thereby reduce the risk of spillage.

Figure 26:
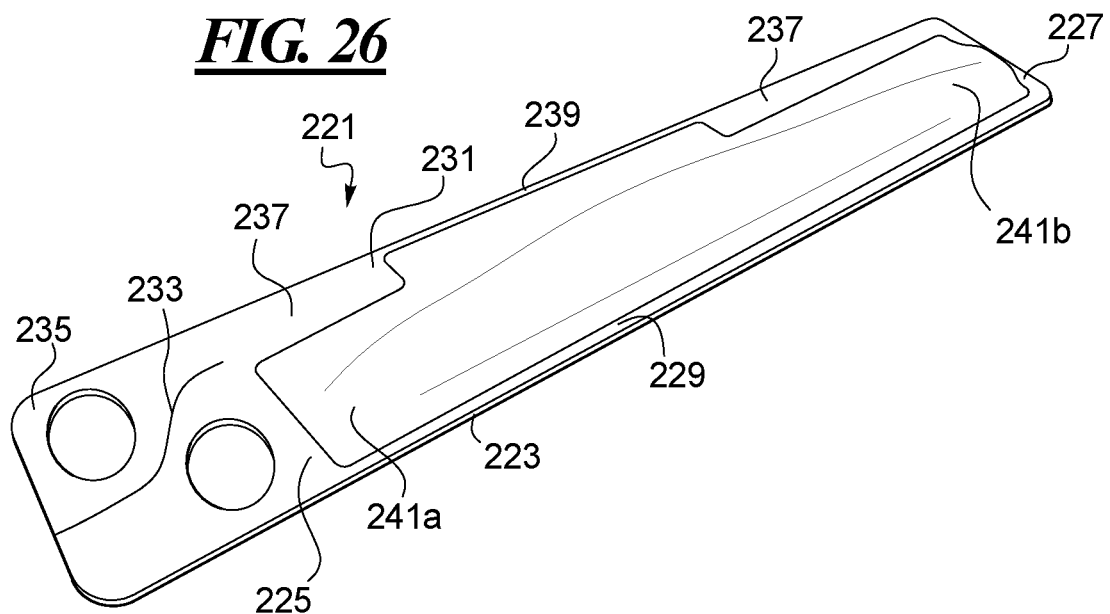
FIG. 26 is a plan view of another embodiment of a medical device package in accordance with the present disclosure.
Figure 27:
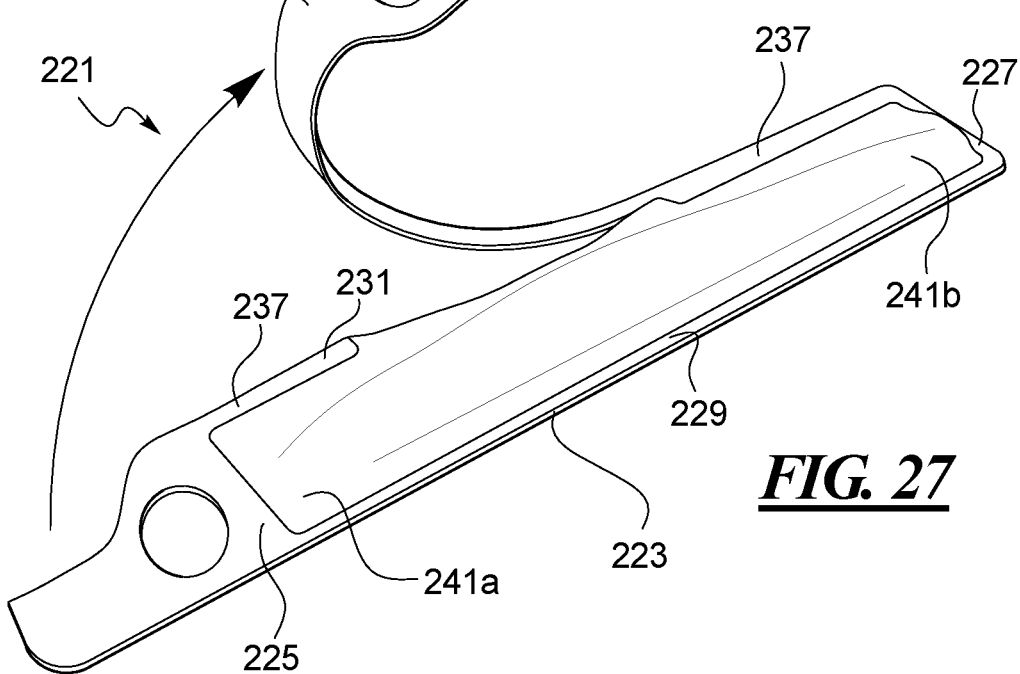
FIG. 27 is a plan view of the medical device package of FIG. 26 shown with the tear initiation element and directional tear element defining an opening of the package.

FIGS. 26 and 27 illustrate an alternative embodiment of a package 221 which is a four-sided sealed package that has similar features to that of package 220. Package 221 includes a peripheral seal 223 that includes a top seal section 225, a bottom seal section 227, a first side seal section 229 and a second side seal section 231. The top seal section 225 may include a tear initiation line 233 and a pull tab 235 for initiating tearing of the package along line 233. The second side seal section 231 may include alternating wide seal portions or projections 237 that project into the cavity of the package and a narrow seal portion 239. A pocket or well 241a is defined in the cavity by a wide seal portion 237, the top seal section 225 and the first side seal section 229. A pocket or well 241b is defined in the cavity by a wide seal portion 237, the bottom seal section 227 and the first side seal section 229. When the package 221 is opened, the liquid may pool in the pockets 241a and 241b to prevent or reduce spillage. For example, if the open package is tilted, the liquid may pool or be collected in pockets 241a and 241b and be prevented from spilling out of the package.

As shown in FIG. 27, the user may open the package 221 by pulling the pull tab 235 to initiate tearing along tear initiation line 233. As the user continues to pull on the pull tab 235, the tear initiation line 233 leads to tearing of the package adjacent to second side seal 231 to form an opening in the package for removing the catheter. When the package is opened, if the package is tilted, the fluid may pool or collect in pockets 241a and 241b thereby reducing the risk of spillage.

The packages disclosed herein may also employ a dual hydration mechanism wherein the package may include a first compartment containing a hydrophilic catheter, and a second compartment containing a vapor donating medium. The compartment containing the catheter may include a hydrophilic catheter that has been pre-hydrated or pre-activated with a hydration medium prior to packaging, or the compartment may include a hydrophilic catheter and loose hydration liquid that contacts the hydrophilic surface of the catheter to hydrate or activate the hydrophilic surface while the catheter is within the package. The compartment containing a vapor donating medium may be at least partially made of a liquid impermeable, vapor permeable material that allows vapor donated from the vapor donating medium to permeate through the liquid impermeable, vapor permeable material to create a vapor atmosphere in the package. The compartment containing the vapor donating medium may be formed by attaching a liquid impermeable, vapor permeable material to a wall or sheet of the package or by inserting a vapor donating medium containing sachet made of liquid impermeable, vapor permeable material into the package. In a package wherein the liquid impermeable, vapor permeable material is attach to the wall of the packaging, the material may be attached so that multiple compartments are formed between the material and the wall. For example, the material may be attached to the wall so as to form two compartments for containing the vapor donating medium. After packaging, the packages may be sterilized by radiation, such as e-beam or gamma radiation.

Referring back to FIG. 1, a liquid impermeable, vapor permeable material or barrier (not shown) may be attached to inner surface 22a of back sheet 15a to define a compartment for the vapor donating medium. The material may be attached by heat sealing or any other suitable manner of attachment. During assembly of the medical device assembly 10a, a vapor donating medium, such as pure water, may be placed in the compartment defined between the inner surface 22a and the liquid impermeable, vapor permeable material. The hydrophilic catheter and a loose hydration liquid may be placed in the cavity or other compartment and the package may be sealed. In the package, the loose hydration liquid contacts the hydrophilic catheter to activate the hydrophilic material of the catheter and the vapor donating medium donates a vapor that permeates through the liquid impermeable, vapor permeable material to create a vapor atmosphere in the package. The vapor atmosphere assists in maintaining the hydrophilic catheter in a hydrated state during storage and distribution of the package.

Figure 28:
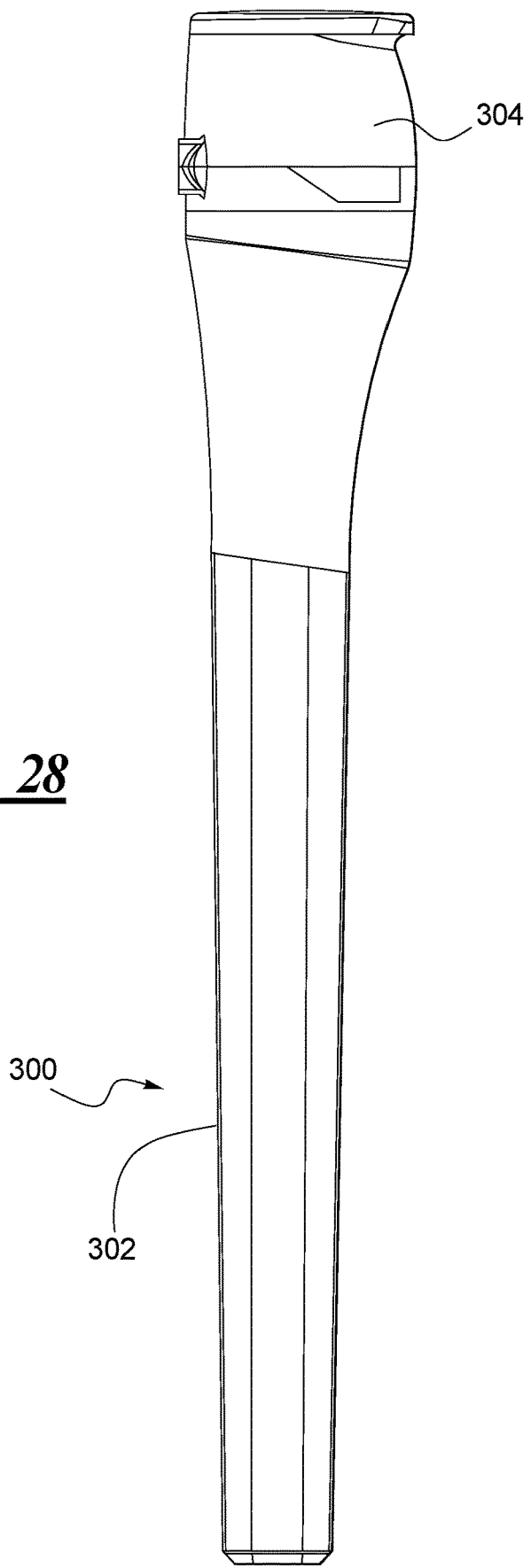
FIG. 28 is a side elevation view of another embodiment of a medical package in accordance with the present disclosure.
Figure 29:
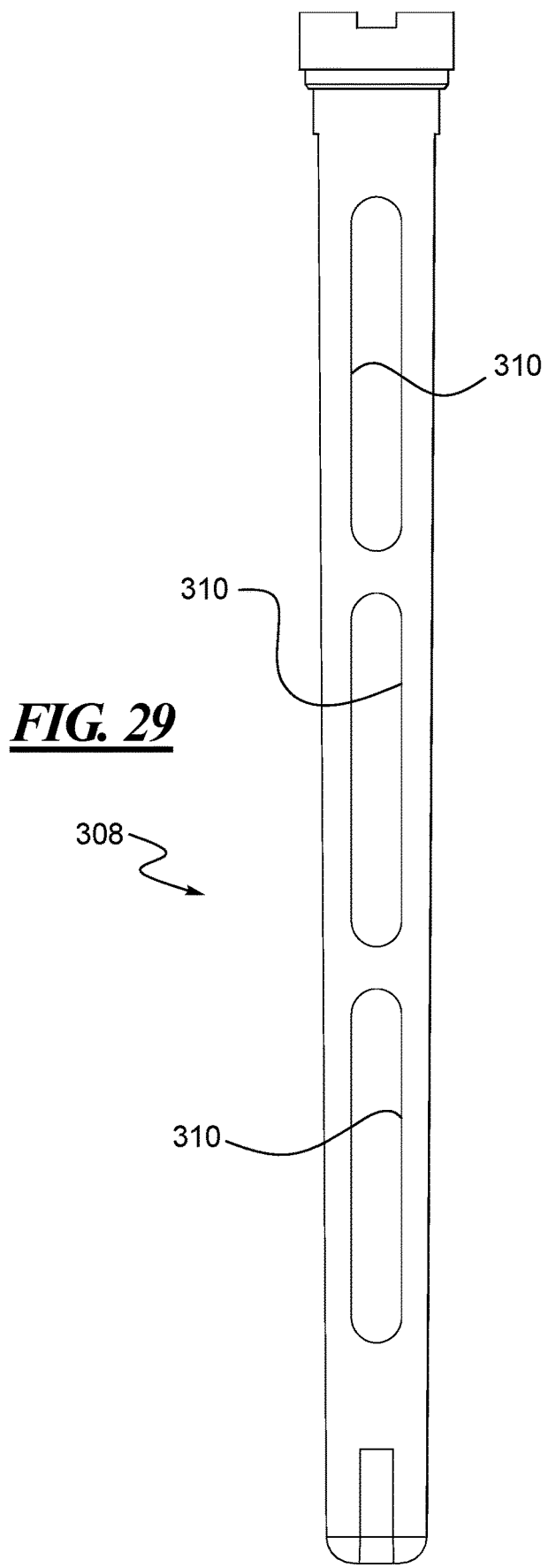
FIG. 29 is a side elevation view of an insert that may be located within the package of FIG. 28.
Figure 30:
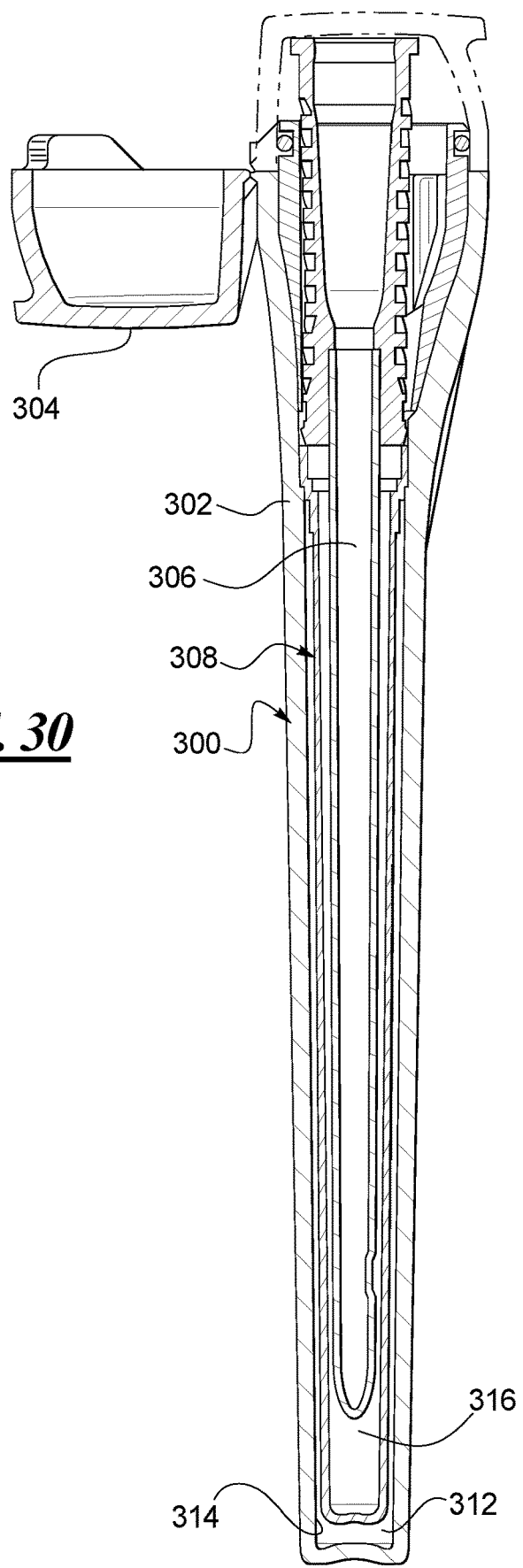
FIG. 30 is a cross-sectional view of the package of FIG. 28.

FIGS. 28-30 illustrate another embodiment of a catheter package wherein dual hydration may be employed. The catheter package 300 includes a body 302 and a cap 304. The body 302 defines a cavity for containing a hydrophilic catheter 306 (FIG. 30). As shown in FIG. 30, the cap 304 may be opened to remove the catheter from the package 300. Referring to FIGS. 29 and 30, the package 300 includes a liner 308 that can be positioned within the body 302. The liner includes openings 310 that are covered with a liquid impermeable, vapor permeable material.

Referring to FIG. 30, during assembly of the package 300, the liner 308 is placed within the body 302. A compartment 312 for containing a vapor donating medium is defined between the liner 308 and an inner surface 314 of the body 302. Additionally, the inner cavity of the liner 308 defines a compartment 316 for containing the hydrophilic catheter 306. During assembly of the package 300, a vapor donating medium, such as pure water, may be placed in the compartment defined between the inner surface 314 of the body 302 and the liner 308. The hydrophilic catheter and a loose hydration liquid may be placed in the other compartment 314 and the cap 304 may be secured to close the package 300. In the package 300, the loose hydration liquid contacts the hydrophilic catheter 306 to activate the hydrophilic material of the catheter and the vapor donating medium donates a vapor that permeates through the liquid impermeable, vapor permeable material covering openings 310 in the liner 308 to create a vapor atmosphere in the package. The vapor atmosphere assists in maintaining the hydrophilic catheter in a hydrated state during storage and distribution of the package.

It should be understood that various changes and modifications to the presently preferred embodiments described herein will be apparent to those skilled in the art. Such changes and modification can be made without departing from the spirit and scope of the invention disclosed herein.

The invention claimed is:

1. A packaged urinary catheter product, comprising:
a package comprising:
a front sheet and a back sheet wherein each of the front sheet and back sheet includes an inner surface facing the other sheet, an outer surface facing the ambient atmosphere, a top edge, a bottom edge and opposed first and second side edges, the front sheet and back sheet being sealed to each other by a peelable continuous peripheral seal so that a gas tight cavity is defined between the front sheet and the back sheet, the peripheral seal having a top seal zone, bottom seal zone, and opposed first and second side seal zones wherein the first side seal zone of the peripheral seal extends along at least a portion of the first side edges of the front and back sheets and the second side seal zone of the peripheral seal extends along the second side edges of the front and back sheets, the front and back sheets being separated to open the package by at least partially peeling the sheets apart along the top seal zone and opposed first and second side seal zones of the peripheral seal;
a first peel-stop located in the first side seal zone of the peripheral seal and a second peel-stop located in the second side seal zone of the peripheral seal, wherein the first and second peel-stops limit peeling of the first and second side seal zones of the peripheral seal;
a urinary catheter within the gas tight cavity of the package;
an amount of hydration liquid in the gas tight cavity of the package; and
pockets defined by the first and second peel-stops, wherein when the package is opened hydration liquid pools in the pockets to reduce spillage of the hydration liquid.

2. The packaged urinary catheter product of claim 1, wherein the first and second peel-stops comprise seal zone portions that requires more force to peel apart than other portions of the seal zone.

3. The packaged urinary catheter product of claim 1, wherein first and second peel-stops comprise widened seal zone portions.

4. The packaged urinary catheter product of claim 1, wherein the peel-stops are positioned so that the package opens to expose only a selected portion of the urinary catheter.

5. The packaged urinary catheter product of claim 4, wherein the selected portion of the urinary catheter comprises a distal end of the urinary catheter.

6. The packaged urinary catheter product of claim 5, wherein the selected portion of the urinary catheter comprises a distal third or less of the urinary catheter.

7. The packaged urinary catheter product of claim 1, wherein the peel-stops are positioned closer to the top seal zone of the peripheral seal than the bottom seal zone of the peripheral seal.

8. The packaged urinary catheter product of claim 5, wherein a distal end of the urinary catheter is adjacent to the top seal zone.

9. The packaged urinary catheter product of claim 1, wherein the top seal zone of the peripheral seal is spaced from the top edges of the front and back sheets such that top portions of the sheets are not sealed together.

10. The packaged urinary catheter product of claim 9, wherein the top seal zone has a non-linear shape.

11. The packaged urinary catheter product of claim 10, wherein the non-linear shape of the top seal zone comprises a chevron shape.

12. The packaged urinary catheter product of claim 1, further including a gripping aid positioned on the urinary catheter.

13. The packaged urinary catheter product of claim 12, wherein the peel-stops are positioned so that the package opens to expose only the portion of the catheter having the gripping aid thereon.

14. The packaged urinary catheter product of claim 13, wherein the gripping aid is positioned on a distal end portion of the urinary catheter.

15. The packaged urinary catheter product of claim 1, wherein the front and back sheets are made from a liquid and gas impermeable material.

16. The packaged urinary catheter product of claim 15, wherein the liquid and gas impermeable material is a polymer/metal laminate.

17. The packaged urinary catheter product of claim 1 further including a plurality of peel-stops.

* * * * *